US007922700B2

(12) United States Patent
Evans et al.

(10) Patent No.: US 7,922,700 B2
(45) Date of Patent: Apr. 12, 2011

(54) PINCH VALVE MECHANISM FOR A MEDICAL FLUID INJECTION DEVICE

(75) Inventors: Alan Evans, Otsego, MN (US); Marty Hieb, St. Louis Park, MN (US); Khoi Le, Chanhassen, MN (US); Chris Lins, Crystal, MN (US); Steven Paul Plager, Eden Prairie, MN (US); Bill West, Eden Prairie, MN (US); Darryl T. Wrolson, Waconia, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 12/261,786

(22) Filed: Oct. 30, 2008

(65) Prior Publication Data

US 2010/0114024 A1 May 6, 2010

(51) Int. Cl.
*A61M 5/00* (2006.01)
*F16K 7/04* (2006.01)

(52) U.S. Cl. ............ 604/250; 604/34; 604/246; 604/67; 251/7; 251/4

(58) Field of Classification Search ................ 604/34, 604/247, 249, 250, 67, 246, 37; 251/7, 4, 251/6, 9
See application file for complete search history.

(56) References Cited

U.S. PATENT DOCUMENTS

| 3,278,153 A | | 10/1966 | Dallas | |
|---|---|---|---|---|
| 3,823,724 A | * | 7/1974 | Davis | 137/15.01 |
| 5,026,020 A | * | 6/1991 | Betush | 251/5 |
| 5,573,515 A | | 11/1996 | Wilson et al. | |
| 7,258,681 B2 | * | 8/2007 | Houde | 604/246 |
| 7,308,300 B2 | * | 12/2007 | Toews et al. | 600/432 |
| 2002/0017299 A1 | * | 2/2002 | Hickle | 128/204.21 |
| 2006/0197040 A1 | | 9/2006 | Brieske | |

FOREIGN PATENT DOCUMENTS

| WO | WO 2004/006994 A1 | 1/2004 |
|---|---|---|
| WO | WO 2007/033103 A1 | 3/2007 |
| WO | WO 2007/062315 A3 | 5/2007 |

OTHER PUBLICATIONS

"ACIST CVi Contrast Delivery System User Manual", ACIST Medical Systems, Inc., Nov. 2005, (91 pages).

(Continued)

*Primary Examiner* — Nicholas D Lucchesi
*Assistant Examiner* — Leah Stohr
(74) *Attorney, Agent, or Firm* — Shumaker & Sieffert, P.A.

(57) ABSTRACT

In general, this disclosure relates to techniques for sealing, or pinching, high-pressure fluid tubing (e.g., braided tubing) that may be used to deliver medical fluid from a powered medical fluid injection device, such as an injector that delivers contrast media and/or saline during angiographic or computed tomography (CT) procedures. In some cases, one or more low-friction, solenoid-based pinch valve mechanisms may be used. One example powered medical fluid injection device comprises an injector head and at least one pinch valve mechanism that is coupled to the injector head. The at least one pinch valve mechanism comprises a plunger, a reciprocating arm driven by the plunger, and a tube pinching area. The at least one pinch valve mechanism, when deactivated by the injector head, is configured to cause the reciprocating arm to pinch fluid tubing that runs through the tube pinching area.

34 Claims, 16 Drawing Sheets

OTHER PUBLICATIONS

Invitation to Pay Additional Fees and Annex to Form PCT/ISA/206 Communication Relating to the Results of the Partial International Search from counterpart application No. PCT/US2009/062396, mailed Apr. 21, 2010, (4 pages).

International Search Report and Written Opinion of international application No. PCT/US2009/062396, mailed Jul. 19, 2010, 19 pp.

Response to Written Opinion dated Oct. 19, 2010, from PCT patent application No. PCT/US2009/062396, filed Oct. 19, 2010, 13 pp.

\* cited by examiner

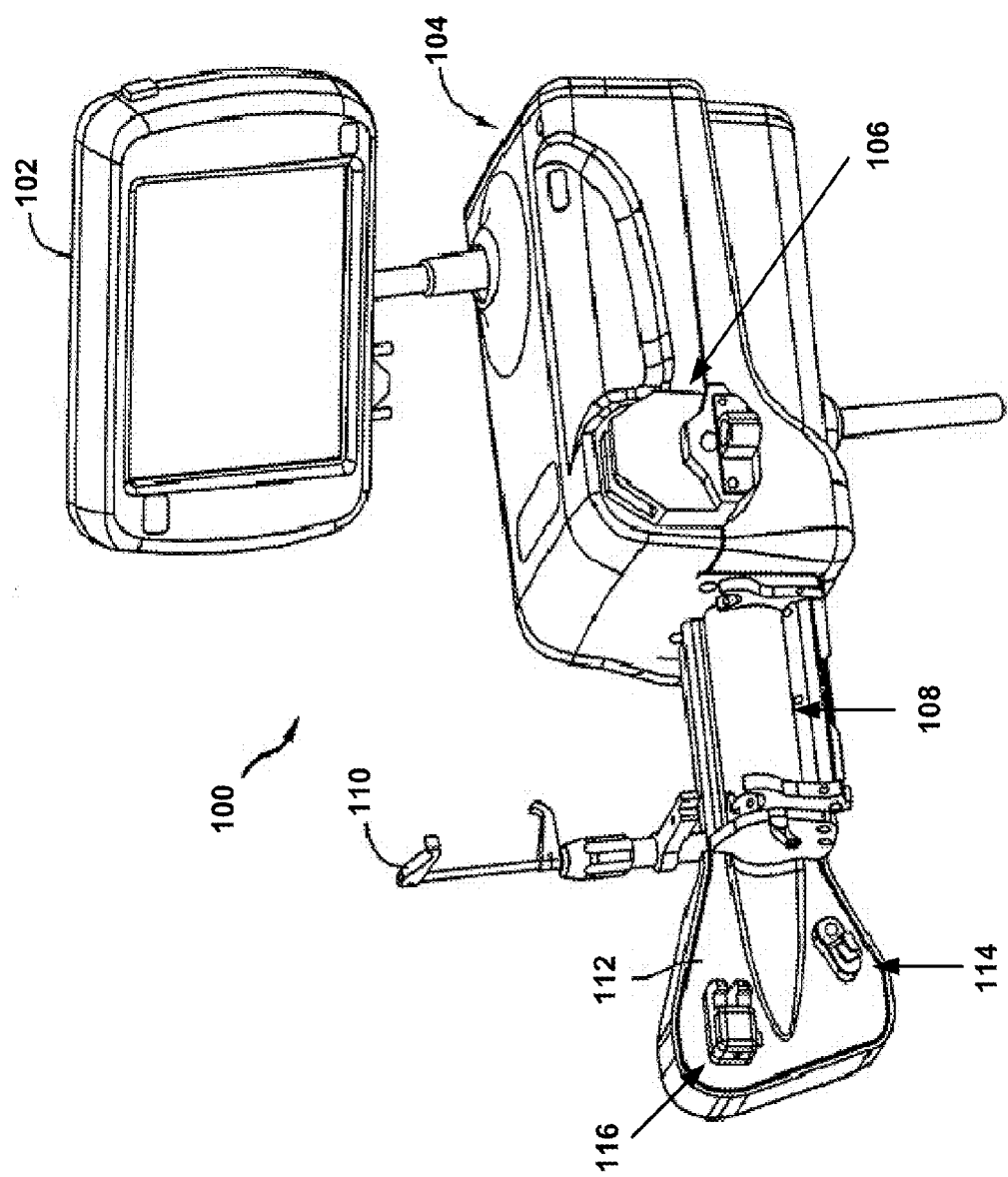

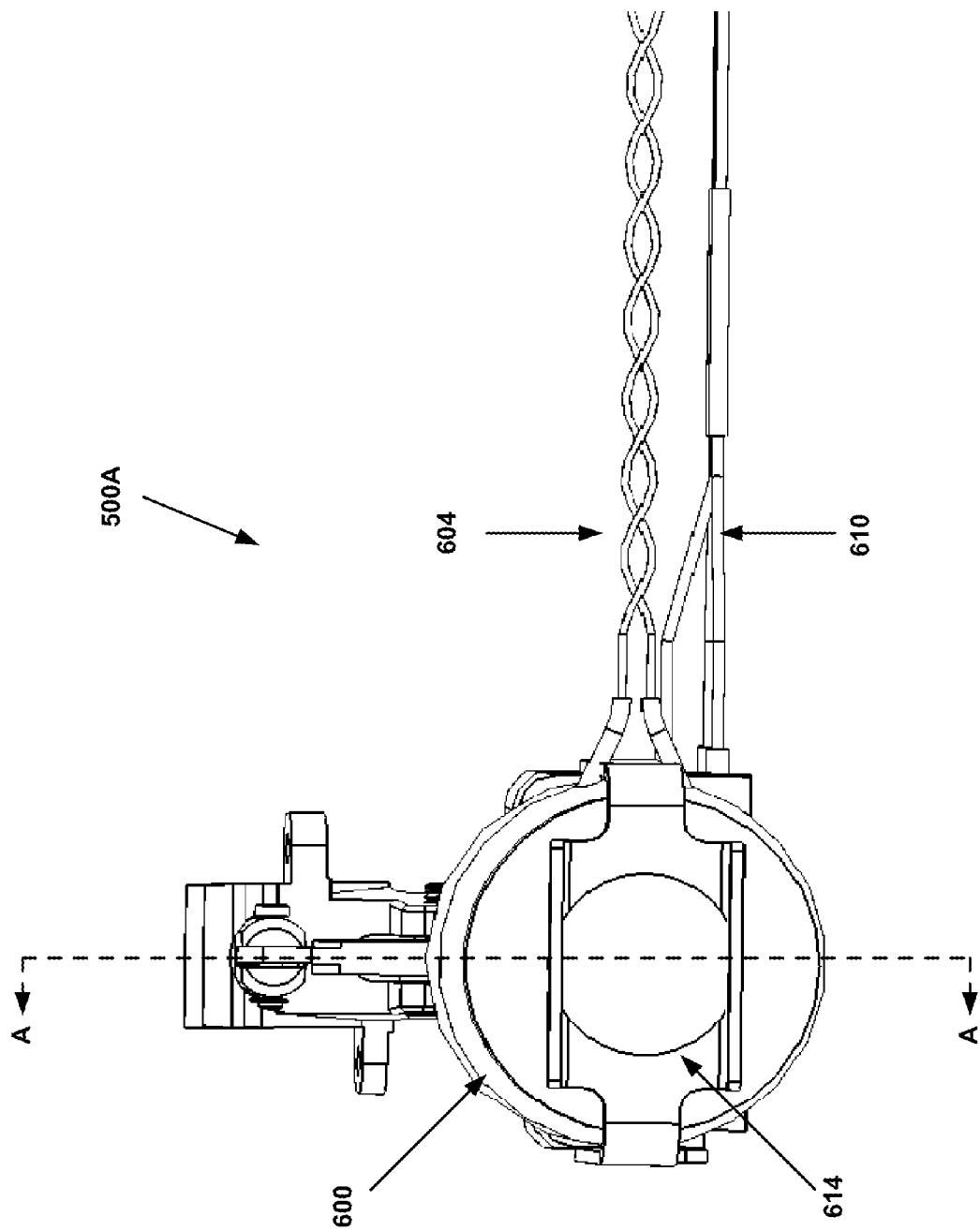

US 7,922,700 B2

PINCH VALVE MECHANISM FOR A MEDICAL FLUID INJECTION DEVICE

TECHNICAL FIELD

This disclosure generally relates to the use of pinch valves within powered medical fluid injection devices.

BACKGROUND

Medical fluid injection devices are typically used to inject medical fluid into a patient. These devices often include one or more reservoirs to hold the medical fluid, and one or more pressurizing units to inject the medical fluid into the patient. For example, a contrast media powered injection device may include a reservoir containing contrast media and a syringe that is used to inject the contrast media into the patient. The contrast media injection device may be used during certain medical procedures, such as an angiographic or a computed tomography (CT) procedure.

Many medical fluid injection devices include one or more syringes to inject fluid. A syringe has a chamber for holding the fluid and a plunger that is moveable within the chamber. The fluid is typically drawn into the chamber from a fluid reservoir when the plunger is moved in a first direction. The fluid is then expelled from the chamber and into the patient, via a catheter, when the plunger is moved in a second, opposite direction. The fluid is delivered at a rate that may be determined by a speed of movement of the plunger.

In many cases, high-pressure tubing (such as high-pressure braided tubing) is used to deliver medical fluid to a syringe from a fluid reservoir, or from the syringe to a patient line. An injection device that has been loaded with a syringe may need to control the flow of fluid through high-pressure tubing into and/or out of the syringe. For example, the injection device may control one or more pinch valve mechanisms to controllably open or seal off the high-pressure tubing, thereby controlling the flow of fluid through the tubing. Typically, higher forces are needed to pinch, and seal off, high-pressure tubing as compared with lower-pressure, or non-braided, soft tubing.

SUMMARY

In general, this disclosure relates to techniques for sealing, or pinching, high-pressure fluid tubing (e.g., braided tubing) that may be used to deliver medical fluid from a powered medical fluid injection device, such as an injector that delivers contrast media and/or saline during angiographic or computed tomography (CT) procedures. In some cases, one or more low-friction, solenoid-based pinch valve mechanisms may be used. A low-friction, solenoid-based pinch valve mechanism may, in some cases, provide certain advantages, such as long life, compact package size, rapid response time, and relatively low cost, as will be described in more detail below.

In one embodiment, a powered medical fluid injection device comprises an injector head and at least one pinch valve mechanism that is coupled to the injector head. The at least one pinch valve mechanism comprises a plunger, a reciprocating arm driven by the plunger, and a tube pinching area. The at least one pinch valve mechanism, when deactivated by the injector head, is configured to cause the reciprocating arm to pinch fluid tubing that runs through the tube pinching area.

In one embodiment, a method comprises receiving a pressurizing unit within a sleeve of a powered medical fluid injection device, and controlling a flow of medical fluid into or out of the pressurizing unit through fluid tubing by at least one pinch valve mechanism, wherein the at least one pinch valve mechanism comprises a plunger, a reciprocating arm driven by the plunger, and a tube pinching area, and wherein the at least one pinch valve mechanism, when deactivated by the powered medical fluid injection device, is configured to cause the reciprocating arm to pinch the fluid tubing that runs through the tube pinching area.

In one embodiment, a pinch valve mechanism comprises a plunger, a reciprocating arm driven by the plunger, and a tube pinching area. When the pinch valve mechanism is deactivated, it may be configured to pinch tubing that runs through the tube pinching area.

The details of one or more embodiments are set forth in the accompanying drawings and the description below. Other features, objects, and advantages will be apparent from the description and drawings, and from the claims.

BRIEF DESCRIPTION OF DRAWINGS

FIG. 1A is a perspective diagram of one embodiment of a powered medical fluid injection device that may be used to control a flow of fluid to and/or from one or more pressurizing units.

FIGS. 6A-6C are perspective diagrams of various views of one of the pinch valve mechanisms shown in FIG. 5, according to one embodiment.

DETAILED DESCRIPTION

Figure 1B:
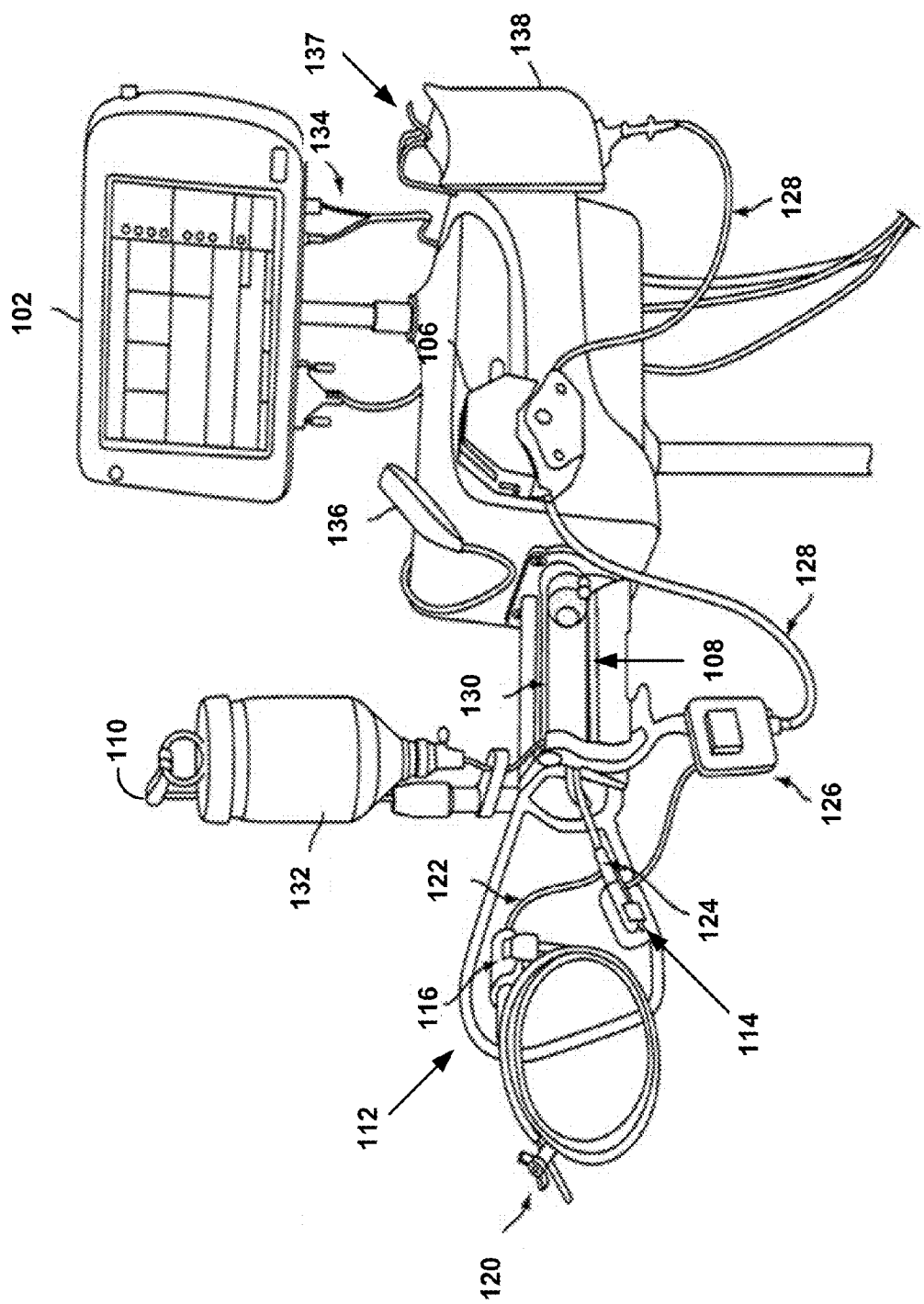
FIG. 1B is a perspective diagram of one embodiment of the powered medical fluid injection device of FIG. 1A connected to various components, including fluid reservoirs and tubing.
Figure 3:
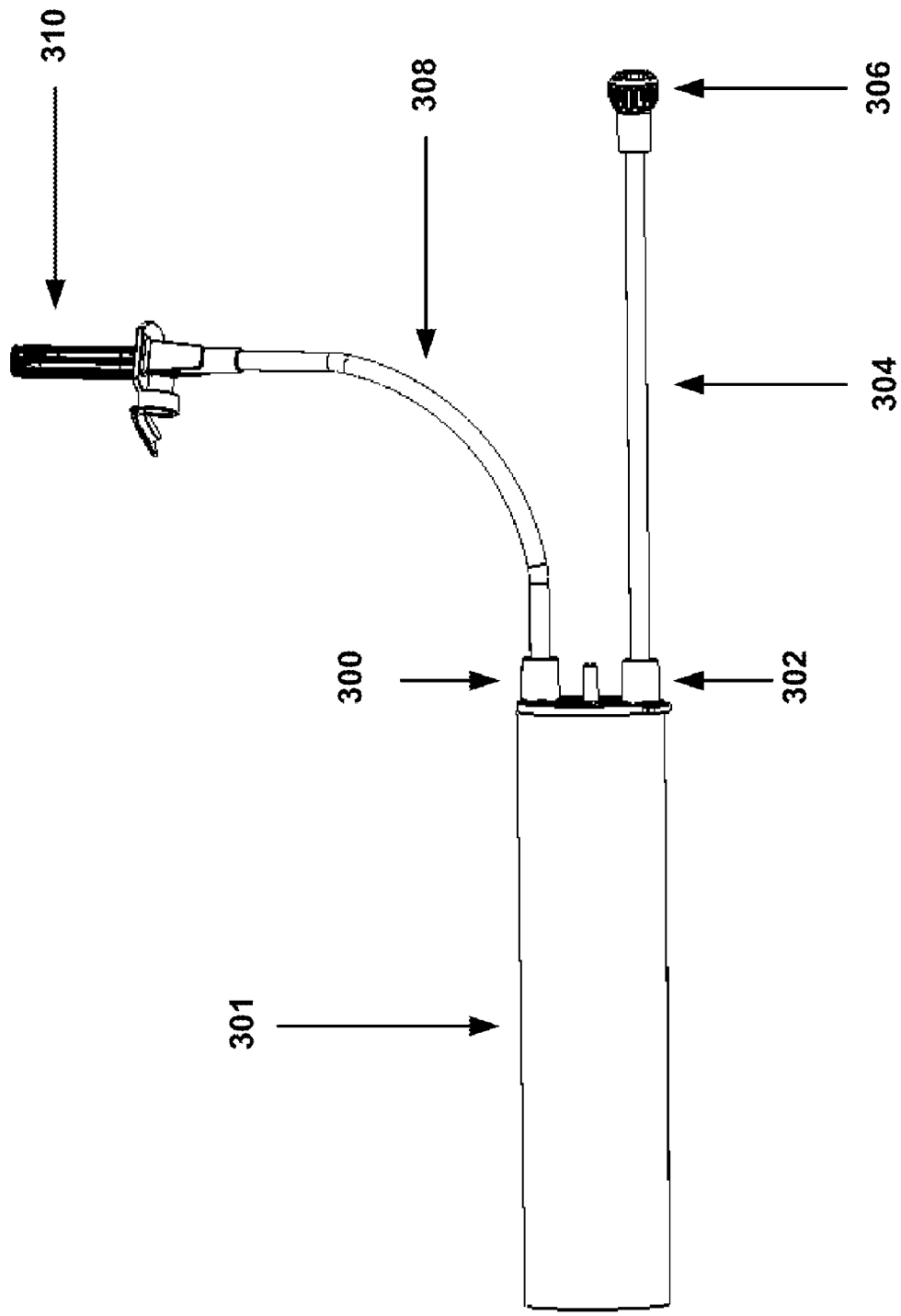
FIG. 3 is a perspective diagram of an example syringe that may be used with a powered medical fluid injection device, according to one embodiment.

FIG. 1A is a perspective diagram of one embodiment of a powered medical fluid injection device 100 that may be used to control a flow of fluid to and/or from one or more pressurizing units, such as a pressurizing unit within a sleeve 108. In the embodiment of FIG. 1A, the pressurizing unit within sleeve 108 is a syringe. In other embodiments, other forms of pressurizing units may be used, including other types of positive displacement pumps. Device 100 is, in some embodiments, used to inject medical fluid, such as contrast media or saline, into a patient during a medical procedure, such as an angiographic or computed tomography (CT) procedure. Device 100 includes a control panel 102, an injector head 104, a sleeve 108 to hold a pressurizing unit, a reservoir holder 110, a module 112, a patient manifold sensor 114, and an air detector 116. Injector head 104 includes a pump 106 and also includes one or more processors used to control and/or monitor injector head 104, control panel 102, the pressurizing unit within sleeve 108, patient manifold sensor 114, and air detector 116 of device 100. Reservoir holder 110 is capable of holding a fluid reservoir that contains an amount of fluid to be drawn into the syringe during operation of device 100. For example, reservoir holder 110 may hold a reservoir of contrast media or diluent. A second reservoir holder (not shown) may hold a diluent (e.g., saline) for use in pump 106. FIG. 3 shows an example of a syringe that may be used within sleeve 108, according to one embodiment. Patient manifold sensor 114 may, in some cases, be connected to a patient manifold, as will be described in reference to FIG. 1B.

An operator of device 100, such as a clinician, may use control panel 102 to set up various parameters and/or protocols to be used for a given injection procedure. For example, the operator may interact with control panel 102 to enter injection parameters for flow rate, maximum injection volume, maximum injection pressure, rise time, or other parameters. In one embodiment, control panel 102 includes a touchscreen panel.

Pump 106 is capable of pumping fluid. In one embodiment, pump 106 is a peristaltic pump. In this embodiment, tubing and a fluid reservoir (not shown) are coupled to and through pump 106. Pump 106 pumps fluid from the fluid reservoir through the tubing towards module 112. In the example of FIG. 1A, both pump 106 and the syringe contained within sleeve 108 are capable of delivering fluid from device 100 into a catheter. Pump 106 is driven by a motor that is part of pump 106, and the plunger within the syringe is driven by a motor assembly, including an actuator, that is part of injector head 104. In one embodiment, injector head 104 includes a processor that drives the motor assembly.

In one embodiment, reservoir holder 110 holds a fluid reservoir that is coupled to input fluid tubing. This input fluid tubing is coupled to the syringe, such that when the plunger within the syringe is moved in a first direction by the motor, fluid is drawn from the reservoir into the syringe. The syringe within sleeve 108 is further coupled to output tubing. When the plunger within the syringe is moved in a second, opposite direction, fluid is expelled out of the syringe into the output tubing. In one embodiment, the syringe is a dual-port syringe, such that the input tubing is coupled to one port of the syringe, and the output tubing is coupled to another port of the syringe. FIG. 3 shows an example of such a dual-port syringe, which will be described in more detail below.

Patient manifold sensor 114 is coupled to a manifold valve (not shown), according to one embodiment. This manifold valve controls flow of fluid from tubing coupled to either the syringe in sleeve 108 or pump 106. In one embodiment, the manifold valve is coupled to output tubing from the syringe and also to tubing that runs through pump 106. Tubing also is coupled between the manifold valve and air detector 116. After passing through air detector 116, the tubing is then coupled to a patient line or catheter (not shown), such that fluid can ultimately be delivered from device 100 to a patient.

The manifold valve held by the patient manifold sensor 114 is capable of controlling the flow of fluid from the syringe and pump 106 to an external catheter. In one embodiment, the manifold valve has a first position that allows only fluid from the syringe to be delivered to the catheter. The manifold valve has a second position that allows only fluid from pump 106 to be delivered to the catheter. In one embodiment, the manifold valve may comprise a spring-biased spool valve, but in other embodiments, other types of valves, including check valves, may also be used. Patient manifold sensor 114 can detect the manifold valve position and report this position to injector head 104 for safety purposes.

Device 100 also includes air detector 116. Tubing that runs from device 100 to an external catheter passes through air detector 116, which is capable of detecting air bubbles or air columns within the tubing. If air detector 116 detects a measurable or otherwise significant amount of air within the tubing, it is capable of generating an alarm signal for injector head 104. In such a case, a warning or alarm message may be displayed to the operator on control panel 102, indicating that air has been detected. In addition, in one embodiment, device 100 may automatically pause, or terminate, a fluid injection procedure if air detector 116 has detected air in the tubing, such that the air is not delivered to the catheter.

In one embodiment, device 100, which may comprise a powered medical fluid injection device, can include at least one pinch valve mechanism that is coupled to injector head 104. The at least one pinch valve mechanism, which will be described in more detail below, may include a plunger, a reciprocating arm driven by the plunger, and a tube pinching area. When the at least one pinch valve mechanism is deactivated by injector head 104, it may be configured to pinch fluid tubing that runs through the tube pinching area. In some instances, the at least one pinch valve mechanism may be used to controllably open or seal off high-pressure tubing that delivers fluid from a pressurizing unit held in sleeve 108 and into a patient line. In such fashion, the pinch valve mechanism can control a flow of fluid through the high-pressure tubing to the patient line. The pinch valve mechanism may open or seal off a portion of the high-pressure tubing that runs through the tube pinching area.

FIG. 1B is a perspective diagram of one embodiment of the powered medical fluid injection device 100 of FIG. 1A connected to various components, including fluid reservoirs and tubing. For example, FIG. 1B shows a first fluid reservoir 132 and a second fluid reservoir 138. First fluid reservoir 132 contains a first fluid, such as contrast media. An operator may hang first fluid reservoir 132 on reservoir holder 110. In some cases, first fluid reservoir 132 may be a glass reservoir, while in other cases, it may be a plastic reservoir. The fluid contained within first fluid reservoir 132 may be drawn through tubing and into a pressurizing unit 130 (e.g., a syringe) that has been inserted into sleeve 108 during operation. During an automatic replenishment operation, device 100 may automatically supply pressurizing unit 130 with an amount of fluid from first fluid reservoir 132.

Second fluid reservoir 138 may contain a second fluid, such as saline. An operator may hang second fluid reservoir 138 on a hook 137. In some cases, second fluid reservoir 138 may be a plastic reservoir, such as a bag. The fluid contained within second fluid reservoir 138 may be drawn through tubing 128 through operation of pump 106.

FIG. 1B also shows that a hand-control device 136 is coupled to control panel 102 via a connector 134. In one embodiment, hand-control device 136 may be connected to another component of device 100 other than control panel 102. As shown in FIG. 1B, hand-control device 136 is coupled to tubing, cabling, or wiring, which connects hand-control device 136 to connector 134. Connector 134 may then be connected to or disconnected from control panel 102. An operator may manipulate hand-control device 136 to control injection of fluid from device 100. For example, the operator may use hand-control device 136 as a variable-rate control device to variably control the rate of flow of fluid from device 100 (e.g., flow of fluid out of pressurizing unit 130). In one embodiment, hand-control device 136 may comprise an electrical device. In one embodiment, hand-control device 136 may comprise a pneumatic device.

Tubing 128 is coupled to a pressure transducer 126. Pressure transducer 126 is also coupled to output, high-pressure tubing 122, which may be connected to a patient line via connector 120. When high-pressure tubing 122 is connected to a patient line (within a patient), pressure transducer 126 is capable of functioning as a hemodynamic monitor for the patient. Pressure transducer 126 converts detected pressures into electrical signals that may be monitored or otherwise used by device 100 or another monitoring device. High-pressure tubing 122 also runs through air detector 116. Air detector 116 is capable of detecting the presence of air (e.g., air bubbles or columns) within fluid that may be flowing through high-pressure tubing 122.

FIG. 1B also shows a manifold valve 124. This manifold valve 124 is connected to high-pressure tubing 122, as well as patient manifold sensor 114. Manifold valve 124 is capable of controlling a flow of fluid from pressurizing unit 130 and/or through pump 106 to high-pressure tubing 122. For example, in one embodiment, when manifold valve 124 is in a first position, fluid may flow from pressurizing unit 130 to high-pressure tubing 122. When manifold valve 124, however, is in a second position, fluid may flow through pump 106, via tubing 128, to high-pressure tubing 122. In one embodiment, manifold valve 124 may allow fluid flow to high-pressure tubing 122 from only one of pressurizing unit 130 or pump 106 at a time.

In one embodiment, as described above, the device may include at least one pinch valve mechanism that is coupled to the injector head. The at least one pinch valve mechanism, which will be described in more detail below, may include a plunger, a reciprocating arm driven by the plunger, and a tube pinching area. When the at least one pinch valve mechanism is deactivated by the injector head, it may be configured to pinch fluid tubing, such as high-pressure tubing 122, that runs through the tube pinching area. The at least one pinch valve mechanism may be located anywhere coupled to the injector head, such as adjacent to manifold valve 124, to control the flow of fluid through high-pressure tubing 122.

As described previously, the powered injection device may include at least one pinch valve mechanism that is coupled to the injector head. The at least one pinch valve mechanism may include a plunger, a reciprocating arm driven by the plunger, and a tube pinching area. When the at least one pinch valve mechanism is deactivated by the injector head, it may be configured to pinch fluid tubing that runs through the tube pinching area, such as a portion of high-pressure tubing 122. In some instances, the at least one pinch valve mechanism may be used to controllably open or seal off high-pressure tubing 122 that delivers fluid from pressurizing unit 130 and into a patient line. In such fashion, the pinch valve mechanism can control a flow of fluid through high-pressure tubing 122 to the patient line.

Figure 2A:
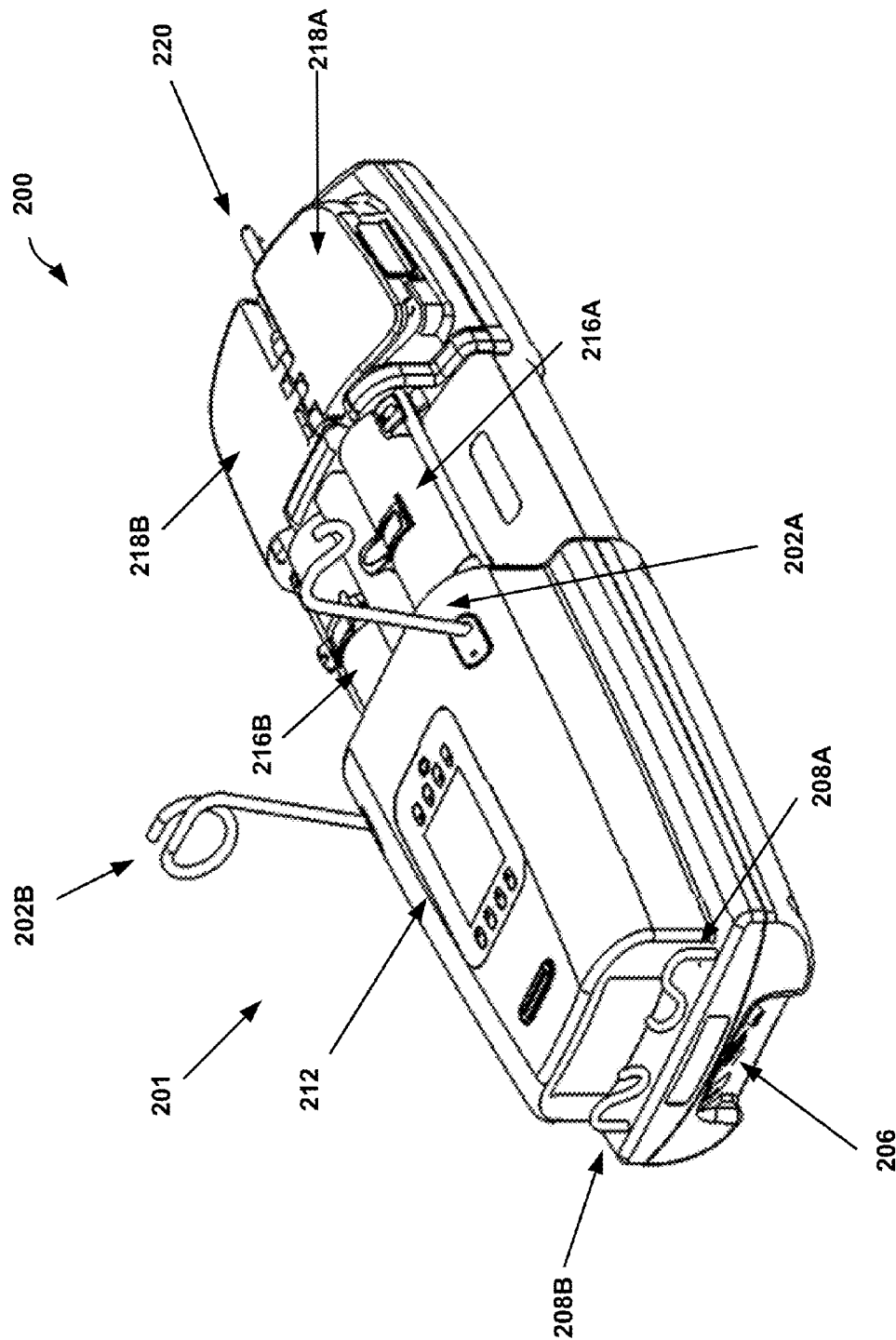
FIGS. 2A-2D are various perspective diagrams of another embodiment of a powered medical fluid injection device that may be used to control a flow of fluid to and/or from one or more pressurizing units.

FIG. 2A is a perspective diagram of another embodiment of a powered injection device 200 that may be used to perform various functions and, when operable, may control a flow of fluid to and/or from one or more pressurizing units. In FIG. 2A, device 200 includes a first primary reservoir holder 202A, a second primary reservoir holder 202B, an electrical connection interface 206, a first backup reservoir holder 208A, a second backup reservoir holder 208B, a control panel 212, a first syringe sleeve 216A, a second syringe sleeve 216B, a first front-end assembly 218A, a second front-end assembly 218B, and a patient connection guide rod 220. In the embodiment of FIG. 2A, the pressurizing units that are used to deliver medical fluid are syringes that are contained within sleeves 216A and 216B. Injector head 201 includes reservoir holder 202A, reservoir holder 202B, connection interface 206, reservoir holder 208A, reservoir holder 208B, and control panel 212. Injector head 201 further includes one or more processors used to control and/or monitor the components of injector head 201 and other components of device 200.

Reservoir holder 202A is capable of holding a first reservoir of medical fluid, while reservoir holder 202B is capable of holding a second reservoir of medical fluid. In one embodiment, reservoir holder 202A holds a reservoir of a first type of fluid, such as contrast media, while reservoir holder 202B holds a reservoir of a second, different type of fluid, such as a diluent (e.g., saline). Different forms of reservoirs (e.g., bottles, bags) may be used with reservoir holders 202A and 202B. Because device 200 may be used to inject medical fluid over multiple patient procedures, the reservoirs held by holders 202A and 202B may need to be replaced over time. Typically, an operator of device 200 manually replaces the reservoirs on holders 202A and 202B. For operator convenience, device 200 additionally includes backup holders 208A and 208B. The operator may store backup fluid reservoirs on holders 208A and 208B. When a reservoir on primary holder 202A or 202B runs empty and needs to be replaced, operator may quickly and easily access a new fluid reservoir from one of backup holders 208A or 208B and attach to primary holder 202A or 202B.

Device 200 includes electrical connection interface 206 to directly or indirectly couple device 200 to an external medical device, such as a medical imaging device. Typically, device 200, when used as a contrast media injection device, works in conjunction with a medical imaging device. For example, device 200 may work in conjunction with a medical imaging device during an angiographic or CT procedure. Connection interface 206 is used to directly or indirectly connect device 200 to such an imaging device. In one embodiment, device 200 may transmit injection and/or control information to an external imaging device via interface 206, and may receive imaging and/or control information from the external imaging device via interface 206, as well.

FIG. 2A shows that device 200 also includes control panel 212. Control panel 212 is located on the top side of example device 200. The operator may interact with control panel 212 to program various injection procedure parameters and/or protocols that may be used for injection procedures. The operator may also use control panel to set up device 200 for use, to begin, pause, resume, or end a procedure, or to view various injection-related information (such as flow rate, volume, pressure, rise time, procedure type, fluid information, and/or patient information). FIG. 2A shows various user-activated buttons on the side of control panel 212. However, in one embodiment, control panel 212 may include a touch-activated screen.

In one embodiment, a separate, larger control panel (not shown) may also be in communication with device 200. In this embodiment, the larger control panel provides similar operator functionality to that provided by control panel 212. However, the larger control panel may be mounted to a rail of a bed on which a patient is lying, or may be mounted to other devices separate from device 200. In one embodiment, the larger control panel looks similar to control panel 102 shown in FIG. 1A.

Device 200 is a dual-syringe device that includes two syringes contained within sleeves 216A and 216B. Both syringes are capable of delivering medical fluid to a patient.

In one embodiment, the syringe within sleeve 216A is capable of drawing in fluid from a fluid reservoir coupled to holder 202A, and the syringe within sleeve 216B is capable of drawing in fluid from a fluid reservoir coupled to holder 202B. For example, these syringes may draw in fluid during a fluid replenishment operation. Each syringe is coupled to a motor/actuator assembly (not shown) that drives a plunger in one of two directions. During a fluid replenishment cycle, for example, a motor/actuator assembly of device 200 may drive a plunger within the syringe in sleeve 216A in one direction to draw fluid from a reservoir coupled to holder 202A into the syringe. During an injection cycle, the motor/actuator assembly of device 200 may drive the plunger within this syringe in the opposite direction to expel fluid. In one embodiment, device 200 contains two distinct motor/actuator assemblies, such that one assembly drives the syringe within sleeve 216A while another drives the syringe within sleeve 216B. These motor/actuator assemblies are part of injector head 201, and may individually be controlled or monitored by the one or more processors included within injector head 201.

Fluid input tubing couples the syringes within sleeves 216A and 216B to the fluid reservoirs and to output lines, according to one embodiment. In one embodiment, the syringes each are dual-port syringes (such as the dual-port syringe shown in FIG. 3). In this embodiment, one syringe port is used for input tubing that is coupled to a fluid reservoir, while the second port is used for output tubing that is operatively coupled to an output (patient) line through assemblies 218A or 218B.

Front-end assembly 218A is associated with sleeve 216A, and front-end assembly 218B is associated with sleeve 216B. Output tubing from the syringe in sleeve 216A runs through assembly 218A and out to a patient line, while output tubing from the syringe in sleeve 216B runs through assembly 218B and out to the patient line. Each assembly 218A and 218B includes a door, or cover, which may be opened and closed by the operator. For the example, the operator may open the door when loading tubing and may be closed upon loading. In one embodiment, each door may be made of a transparent or translucent material, such that the operator may see inside the contents of the assembly 218A or 218B even when the door is closed.

In one embodiment, each front-end assembly 218A and 218B includes air detectors and valve components (not shown). Air detectors are used to detect air bubbles or air columns within the fluid tubing that is used. The valve components are used to allow or restrict fluid flow through tubing. For example, when pinch valves are used, the valves pinch fluid tubing to restrict fluid flow in one state, but stay open to allow fluid flow in another state. Various different forms of valves may be used within assemblies 218A and 218B. In addition, various different forms of air detectors (e.g., ultrasonic, optical) may be used, as well.

In one embodiment, the input and output tubing that is coupled to the syringe in sleeve 216A runs through front-end assembly 218A, and the input and output tubing that is coupled to the syringe in sleeve 216B runs through front-end assembly 218B. In this embodiment, each assembly 218A and 218B contains a first pinch valve and a first air detector coupled to the input tubing for the respective syringe, and further contains a second pinch valve and a second air detector coupled to the output tubing for the respective syringe. These components are more clearly shown in FIG. 2D and will be discussed in more detail below.

Figure 4:
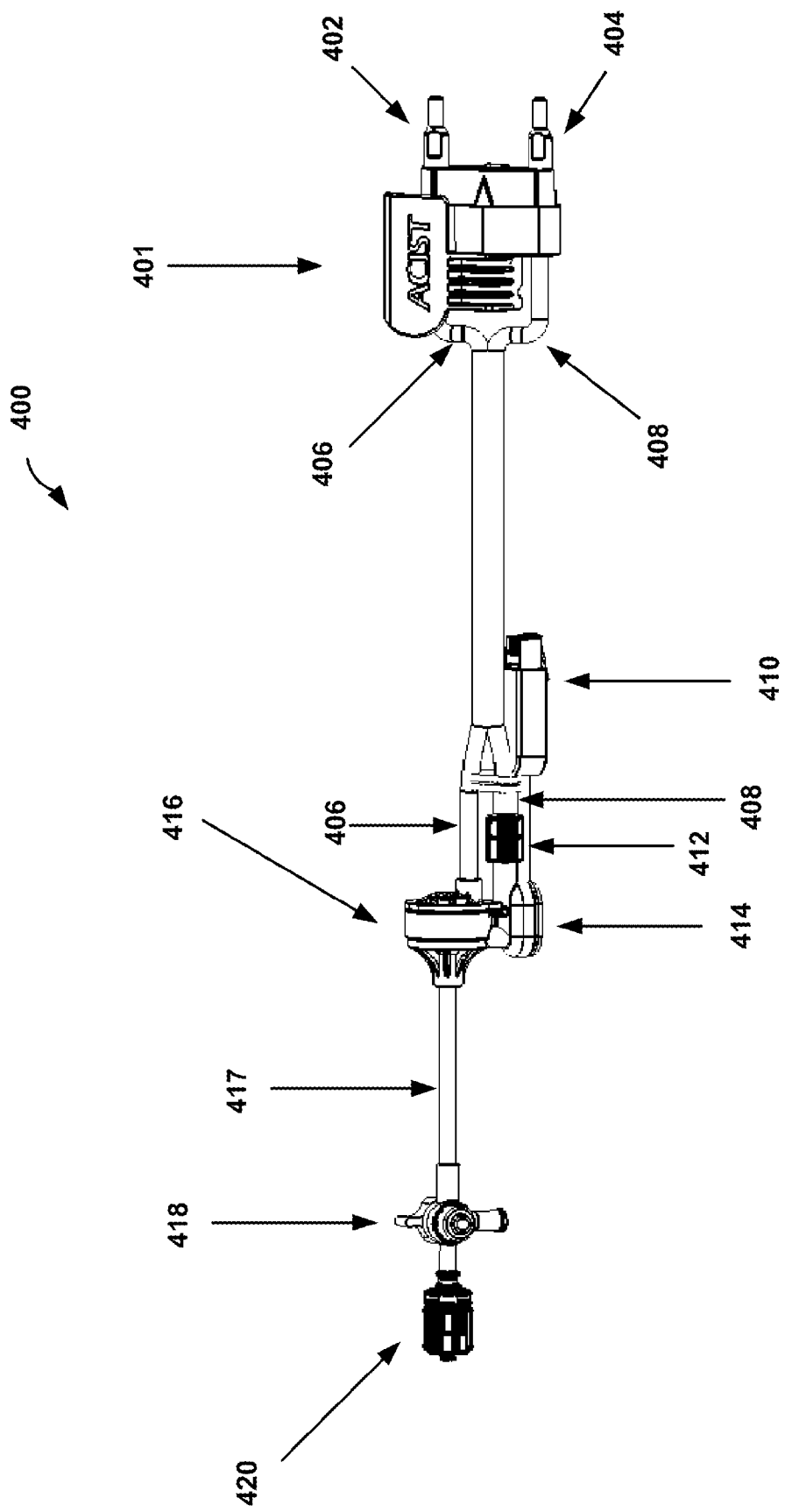
FIG. 4 is a perspective diagram of a patient line that may be used with a powered medical fluid injection device, according to one embodiment.

FIG. 2A also shows a patient connection guide rod 220. The output tubing from syringes 216A and 216B run through front-end assemblies 218A and 218B, respectively, and are then coupled to a patient line, or kit (not shown). The patient line is a single-use line, according to one embodiment, that is used for a single patient procedure. Each patient line may be connected to and disconnected from the output tubing running through front-end assemblies 218A and 218B. The patient line is connected to the output tubing via connection guide rod 220, according to one embodiment. The patient line may slide over connection guide rod 220 in order to become coupled with the output tubing. In one embodiment, the patient line includes two tubing elements, each element corresponding to one of the output tubing elements of the syringe in sleeve 216A or 216B. An example patient line is shown in FIG. 4 and will be discussed in more detail below.

In one embodiment, a medical fluid injection device, such as device 200, may include a plurality of pressurizing units, including three or more pressurizing units. Each of these pressurizing units may be included within a separate sleeve during operation. In some cases, multiple pressurizing units may contain the same type of fluid. For example, a first pressurizing unit may contain contrast media, a second pressurizing unit may contain a diluent (e.g., saline), and a third pressurizing unit may contain contrast media. In this scenario, the third pressurizing unit may comprise a backup, or secondary, source of contrast media. In this example, the first and third pressurizing units may both be coupled to a common front-end assembly, such as a front-end assembly similar to 218A or 218B.

Figure 2B:
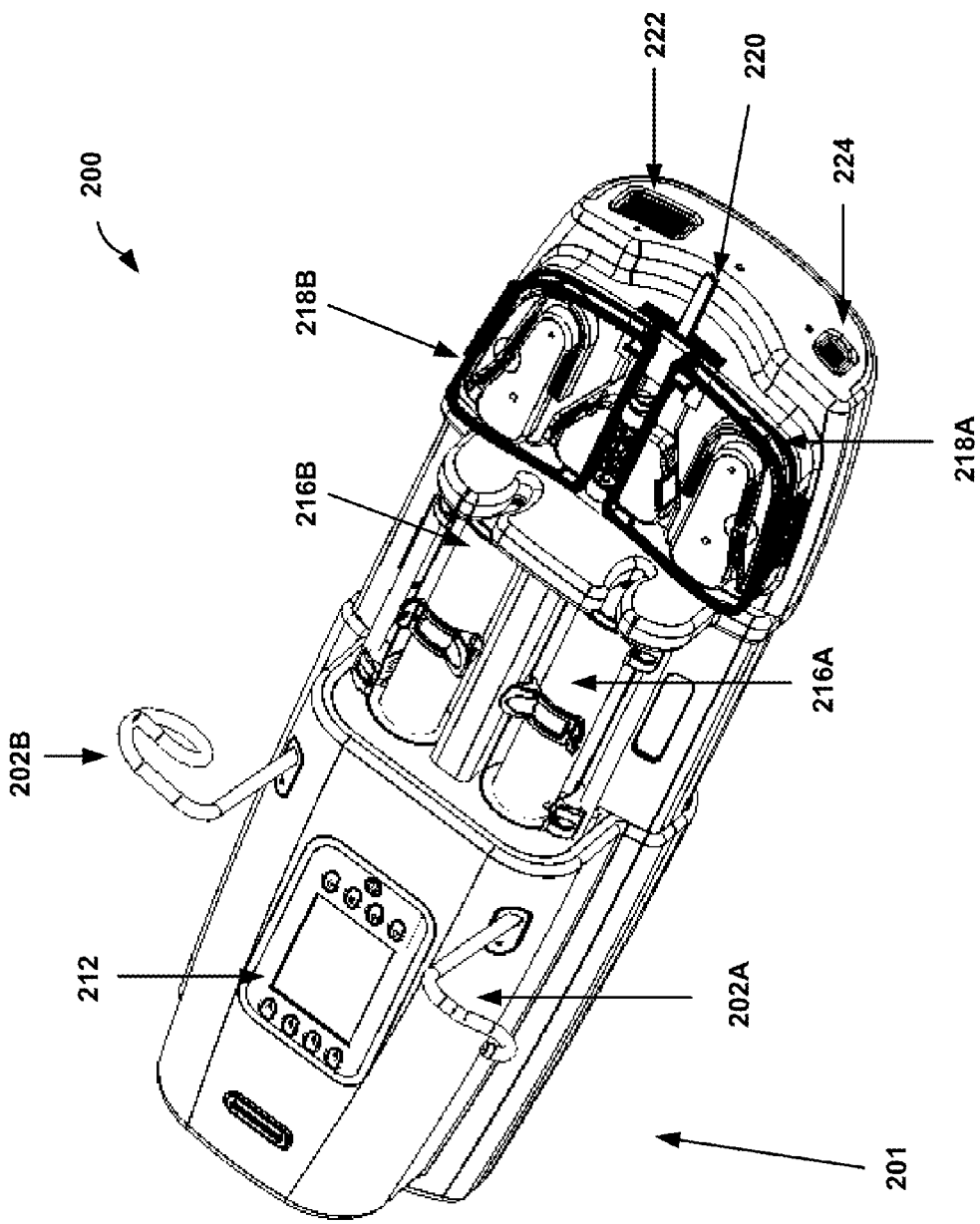

FIG. 2B is another perspective diagram of device 200 shown in FIG. 2A. In FIG. 2B, sleeves 216A and 216B, along with front-end assemblies 218A and 218B, can be more clearly seen. Although the doors of assemblies 218A and 218B are closed in the example of FIG. 2B, they are made of a semi-transparent material, such that the interior pinch valve and air detector components may be more clearly seen. FIG. 2B also shows connection ports 222 and 224. In one embodiment, a pressure transducer connector (such as one coupled to connector 410 shown in FIG. 4), may be connected to connection port 224. The pressure transducer connector is operatively coupled to a pressure transducer, which measures patient hemodynamic signals on the patient line. By connecting a pressure transducer to connection port 224, device 200 is capable of utilizing and processing hemodynamic pressure signals of a patient that are detected in the patient line.

Device 200 also includes connection port 222, which may be connected to a hand-control device (not shown). In one embodiment, the hand-control device is a disposable component that may be used by the operator for a single patient procedure. The hand-control device may control the operation of one or both of syringes in sleeves 216A and 216B. For example, the operator may push a button or otherwise interact with the hand-control device to cause a motor/actuator assembly to inject fluid from the syringe in sleeve 216A, and may push another button or otherwise interact with the hand-control device to cause a motor/actuator assembly to inject fluid from the syringe in sleeve 216B. Thus, if the syringe in sleeve 216A contains contrast media, and the syringe in sleeve 216B contains a diluent, the operator may push one button on the hand-control device to inject contrast into the patient line, and may push another button to inject saline. In one embodiment, the hand-control device contains variable-rate functionality, such that the harder the operator pushes on a button or actuates a component, the greater the flow rate of injected fluid from the syringe in sleeve 216A or 216B.

Figure 2C:
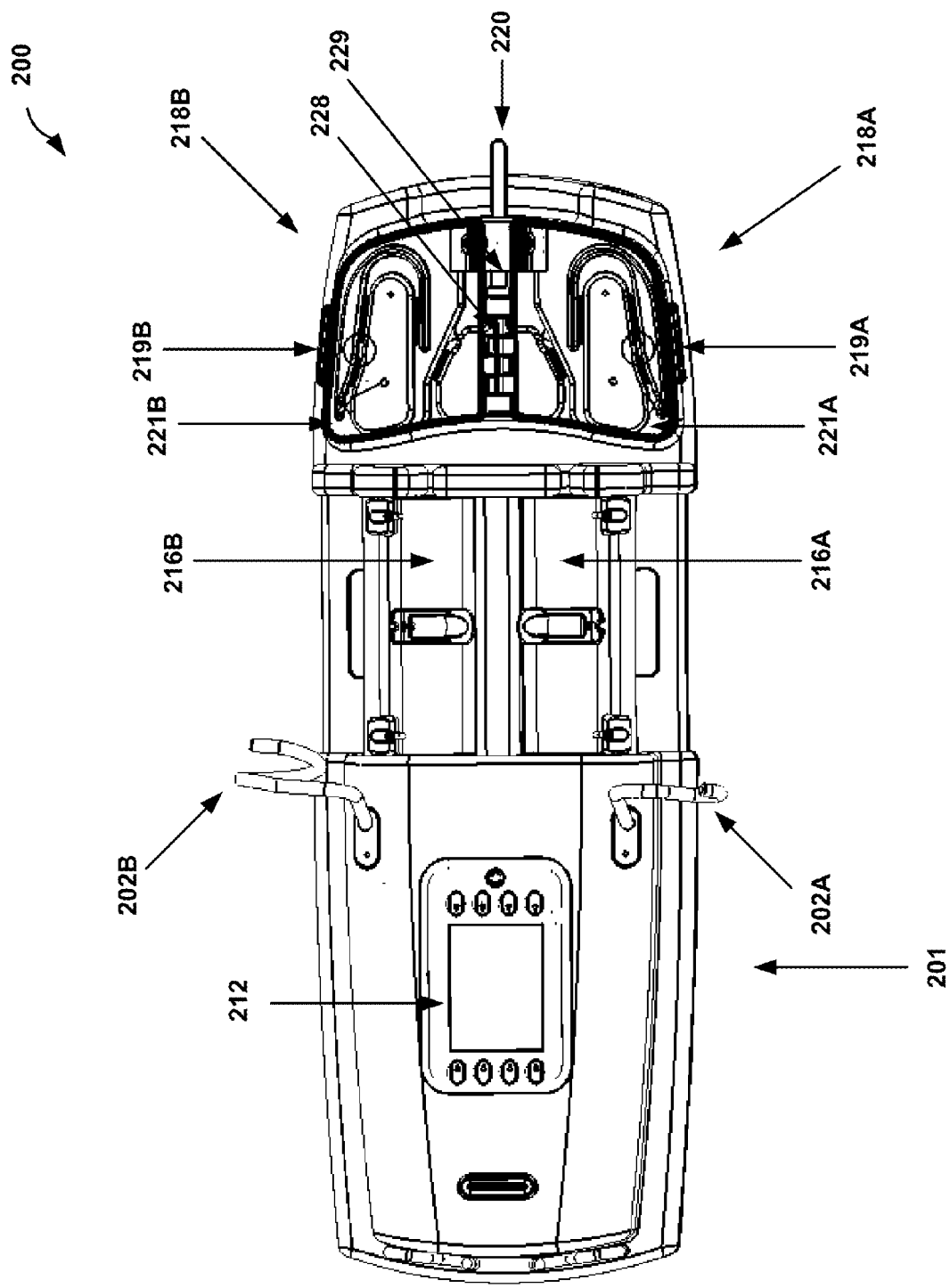

FIG. 2C is another perspective diagram of device 200. FIG. 2C shows a top view of device 200, according to one embodiment.

FIG. 2C also shows doors 221A and 221B on front-end assemblies 218A and 218B, respectively. As noted above, in one embodiment, each of assemblies 218A and 218B include a moveable door 221A and 221B, respectively. Door 221A covers assembly 218A, and door 221B covers assembly 218B. In the embodiment of FIG. 2C, doors 221A and 221B are made of a transparent, or semi-transparent, material, such that an operator may see the contents of assemblies 218A and 218B (which are shown in more detail in FIG. 2D). Door 221A includes a handle 219A, and door 221B includes a handle 219B. The operator may utilize handles 219A and 219B to open and close doors 221A and 221B, respectively. Doors 221A and 221B are coupled to one or more hinges 228, which allow doors 221A and 221B to be opened and closed.

Also shown in FIG. 2C is a pivot pin 229. Pivot pin 229 is inserted through hinges 228, according to one embodiment, to securely allow doors 221A and 221B to be freely opened and closed by an operator. Doors 221A and 221B pivot about an axis that runs through pivot pin 229.

In one embodiment, pivot pin 229 is screwed into place. Pivot pin 229 may also be removed by an operator. For example, the operator may unscrew pivot pin 229 and remove it from front-end assemblies 218A and 218B. After pivot pin 229 has been removed, doors 221A and 221B may also be removed from assemblies 218A and 218B. For example, the operator may choose to remove doors 221A and 221B if the operator wishes to clean or replace doors 221A and 221B.

Figure 2D:
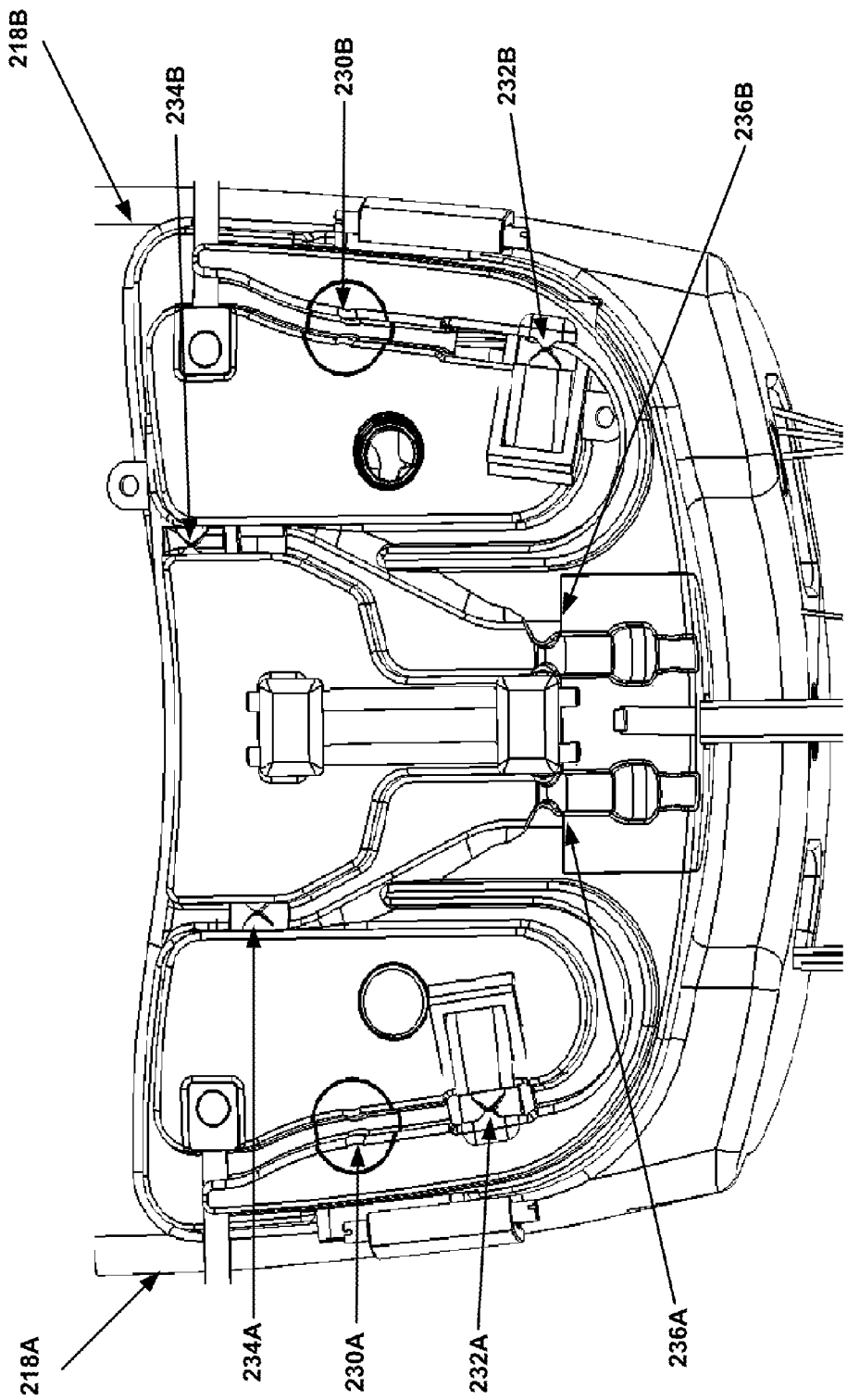

FIG. 2D is a perspective view of front-end assemblies 218A and 218B shown in more detail, according to one embodiment. Although doors 221A and 221B are not shown in FIG. 2D, they are made of a transparent, or semi-transparent, material, such that the contents of assemblies 218A and 218B may be more clearly seen by an operator, even when doors 221A and 221B are closed.

Front-end assembly 218A includes a first air detector 230A, a first pinch valve 232A, a second pinch valve 234A, and a second air detector 236A. Input tubing from a reservoir on holder 202A runs through air detector 230A and pinch valve 232A and into a syringe in sleeve 216A via a first syringe port, according to one embodiment. Output tubing coupled to a second syringe port of the syringe in sleeve 216A runs through pinch valve 234A and air detector 236A and is then coupled an external patient line, or kit (such as the one shown in FIG. 4). Air detector 230A is used to detect air bubbles or columns within the input tubing, and air detector 236A is used to detect air bubbles or columns within the output tubing. Air detectors 230A and 236A may comprise acoustic-based, optical-based, or other forms of air detectors.

If either or both of air detectors 230A and 236A detect a measurable amount of air in the input and/or output tubing, these detectors may propagate signals to injector head 201 of device 200. One or more processors of injector head 201 may process these received signals. Injector head 201 may provide a warning message or alert to the operator via control panel 212, such that the operator may take appropriate action. Injector head 201 may also, in one embodiment, automatically pause or terminate any injection of fluid from the syringe in sleeve 216A if air has been detected in the input and/or output tubing, by controlling operation of the motor/actuator assembly driving the syringe.

Pinch valve 232A controls a flow of fluid from input tubing into the syringe in sleeve 216A. Injector head 201 controls the operation of pinch valve 232A. When injector head 201 opens pinch valve 232A, fluid may flow from the reservoir connected to holder 202A and into the syringe. When pinch valve 232A is closed, no fluid flow is permitted within the input tubing. For example, when injector head 201 is supplying the syringe with fluid, it may open pinch valve 232A to allow fluid flow in the input tubing, but it may also close pinch valve 234A, to prohibit any fluid flow in the output tubing. The plunger within the syringe may be moved in a first direction (by the motor/actuator assembly) to supply fluid to the syringe. When a fluid injection occurs, the motor/actuator assembly will move the plunger within the syringe in a second, opposite direction. Injector head 201 may close pinch valve 232A during an injection procedure, to prohibit fluid flow in the input tubing. However, injector head 201 may open pinch valve 234A, to allow fluid flow in the output tubing during such a procedure. In such fashion, injector head 201 utilizes pinch valves 232A and 234A to control fluid flow in the input and output tubing during various operations (e.g., replenishment and injection operations).

In one embodiment, pinch valves 232A and 234A are solenoid-based pinch valves. In other embodiments, other forms of pinch valves 232A and 234A may be used, such as pneumatic-based valves. In one embodiment, pinch valves 232A and 234A have default states in the closed position. Thus, when device 200 is neither supplying fluid into nor injecting fluid from the syringe in sleeve 216A, both pinch valves 232A and 234A are closed. Pinch valves 232A and 234A may then be opened by device 200 when energy is actively applied to pinch valves 232A and/or 234A. When no energy is applied to pinch valves 232A and/or 234A, they return to a default, closed position. Thus, if there are any power failures to device 200, valves 232A and 234A will return to closed position. This may help improve the safety of device 200.

Similarly, front-end assembly 218B includes a first air detector 230B, a first pinch valve 232B, a second pinch valve 234B, and a second air detector 236B. Input tubing from a reservoir connected to holder 202B runs through air detector 230B and pinch valve 232B and into a first syringe port of the syringe in sleeve 216B. Output tubing coupled to a second syringe port of the syringe runs through pinch valve 234B and air detector 236B, and may then be coupled to a patient line. The components within device 218B function similarly to those contained within device 218A as described above, according to one embodiment.

Figure 5:
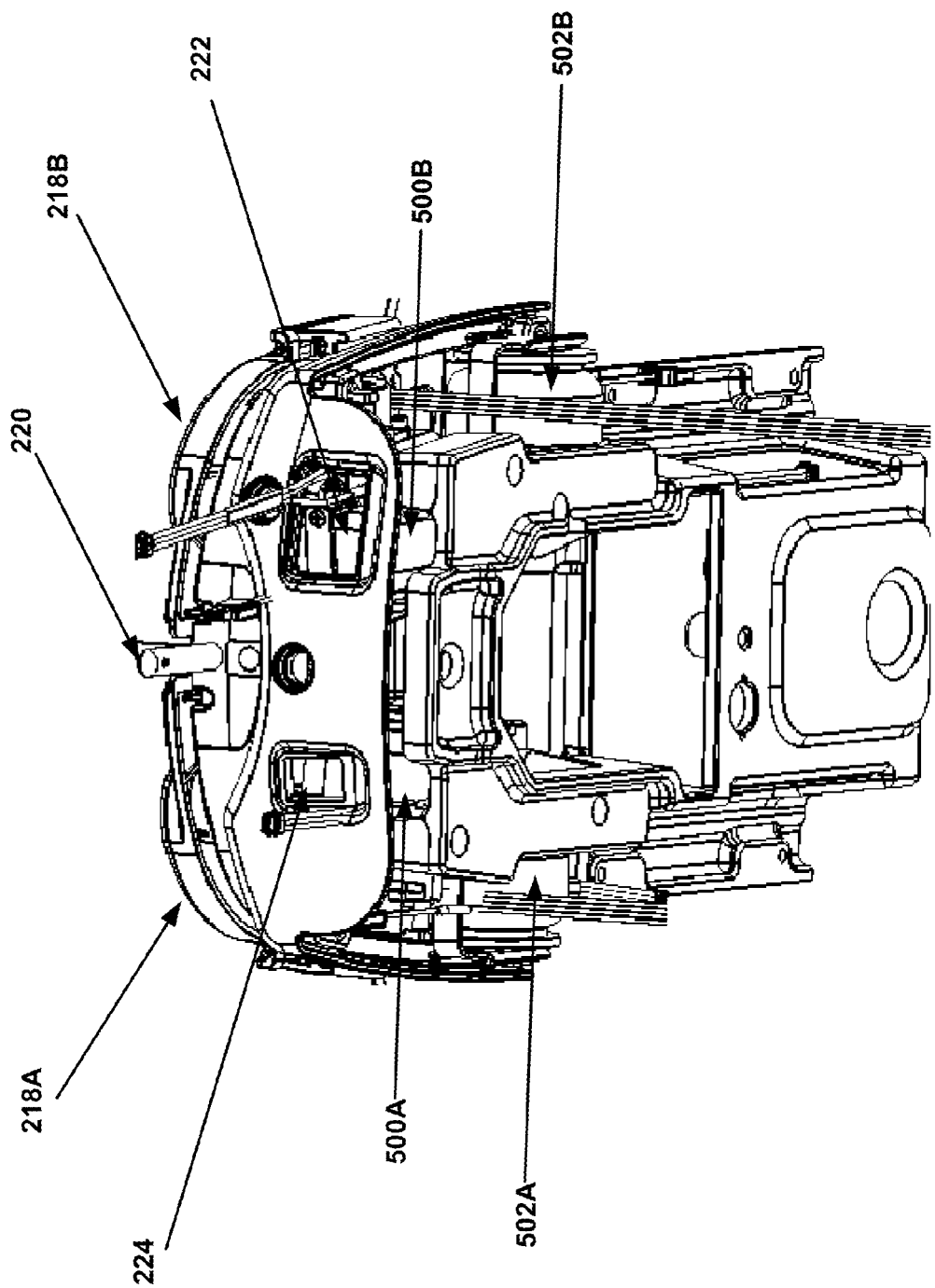
FIG. 5 is a perspective diagram of a bottom view of a portion of the injector head shown in FIG. 2D, according to one embodiment.

In one embodiment, device 200, which may comprise a powered medical fluid injection device, can include at least one pinch valve mechanism that is coupled to injector head 201. The at least one pinch valve mechanism, which will be described in more detail below, may include a plunger, a reciprocating arm driven by the plunger, and a tube pinching area. When the at least one pinch valve mechanism is deactivated by injector head 201, it may be configured to pinch fluid tubing that runs through the tube pinching area. As will be described below, FIG. 5 shows an example of four such pinch valve mechanisms 500A, 500B, 502A, and 502B. These pinch valve mechanisms 500A, 500B, 502A, and 502B may be coupled to, or otherwise include, pinch valves 232A, 232B, 234A, and 234B, which each comprise a corresponding tube pinching area.

In one embodiment, one or more of the pinch valve mechanisms may comprise a solenoid-based pinch valve mechanism. In some instances, the at least one pinch valve mechanism, when activated by injector head 201, may be configured to open a path in the fluid tubing that delivers medical fluid to one or more pressurizing units (e.g., syringes) contained within sleeve 216A and/or sleeve 216B, such as during a fill operation. In these instances, injector head 201 may activate the at least one pinch valve mechanism to allow a pressurizing unit to be filled with fluid from a fluid reservoir.

In some instances, one or more additional pinch valve mechanisms, when activated by injector head 201, may be configured to open a path in the fluid tubing that delivers medical fluid from one or more pressurizing units contained within sleeve 216A and/or sleeve 216B to an external patient line, such as during an injection procedure. In these instances, injector head 201 may activate the one or more additional pinch valve mechanisms to allow fluid in a pressurizing unit to be injected into the patient line.

As noted earlier, various pinch valve mechanisms (such as those shown in FIG. 5) may be coupled to the pinch valves 232A, 232B, 234A, and 234B shown in FIG. 2D. As described previously, pinch valves 232A, 232B, 234A, and 234B may control fluid flow through fluid tubing that runs into or out of a pressurizing unit within sleeve 216A or sleeve 216B. In some instances, a first pinch valve mechanism may be coupled to first fluid tubing that runs into a first pressurizing unit, and a second pinch valve mechanism may be coupled to second fluid tubing that runs out of the first pressurizing unit. The first pressurizing unit may be, for example, contained within sleeve 216A. Injector head 201 may control the first pinch valve mechanism to either open or seal off a flow of fluid through the first fluid tubing and into the first pressurizing unit (e.g., from a fluid reservoir). For example, injector head may activate the first pinch valve mechanism to open a path in the first fluid tubing, such that medical fluid is permitted to flow in the path of the first fluid tubing and into the first pressurizing unit. Similarly, injector head 201 may control the second pinch valve mechanism to either open or seal off a flow of fluid through the second fluid tubing and out of the first pressurizing unit, such as into a patient line.

A third pinch valve mechanism may be coupled to third fluid tubing into a second, separate pressurizing unit, and a fourth pinch valve mechanism may be coupled to fourth fluid tubing out of the second pressurizing unit. The second pressurizing unit may be, for example, contained within sleeve 216B. Injector head 201 may control the third pinch valve mechanism to either open or seal off a flow of fluid through the third fluid tubing and into the second pressurizing unit (e.g., from a fluid reservoir). Similarly, injector head 201 may control the fourth pinch valve mechanism to either open or seal off a flow of fluid through the fourth fluid tubing and out of the second pressurizing unit, such as into a patient line.

FIG. 3 is a perspective diagram of an example syringe 301 that may be used within device 200, according to one embodiment. Syringe 301 may be loaded in either sleeve 216A or 216B. If syringe 301 is loaded into sleeve 216A, it may be coupled to a fluid reservoir connected to holder 202A (FIG. 2A), and may further be coupled to a patient line (FIG. 4).

Syringe 301 is a dual-port syringe in the example of FIG. 3. Input port 300 is coupled to input tubing 308, and output port 302 is coupled to output tubing 304. Input tubing is coupled to a connector 310, which may be connected to a fluid reservoir in holder 202A, assuming syringe 301 is loaded into sleeve 216A. For example, if connector 310 is a spike, the spike may be inserted into a bottle of medical fluid connected to holder 202A. Output tubing 304 is coupled to a connector 306, which couples output tubing 304 to a separate patient line. In one embodiment, connector 306 is a Luer-type connector.

Fluid is drawn from the fluid reservoir into port 300 of syringe 301 via input tubing 308. Fluid is expelled from port 302 of syringe 301 into output tubing 304. Input tubing 308 may run through air detector 230A and pinch valve 232A (FIG. 2D) of front-end assembly 218A, which was described in more detail above, while output tubing 304 may run through pinch valve 234A and air detector 236A. In one embodiment, syringe 301, along with input tubing 308, connector 310, output tubing 304, and connector 306, are disposable, multi-use components. That is, these components may be used within device 200 over multiple uses or patient procedures before they are disconnected from device 200 and disposed of. In another embodiment, these components are disposable, single-use components, meaning that they are disposed of after a single patient procedure.

In one embodiment, syringe 301 may also be used in device 100 (FIG. 1A). When used in device 100, connector 310 would be connected to a fluid reservoir on holder 110, and output tubing 304 would run through patient manifold sensor 114.

FIG. 4 is a perspective diagram of a patient line 400 that may be used with injection device 200 shown in FIGS. 2A-2C, according to one embodiment. Patient line 400 includes an assembly 401, a valve 416, a stopcock 418, and a connector 420. Patient line 400 is used to couple device 200 with a catheter that is used to deliver medical fluid to a patient.

Assembly 401 includes a first connector 402 and a second connector 404. When assembly 401 is coupled to device 200, connector 402 is connected with a connector for output tubing that is coupled to one of the syringes in sleeves 216A or 216B, while connector 404 is connected with a connector for output tubing that is coupled to the other syringe. For example, connector 402 may be connected to connector 306 (FIG. 3), which is coupled to output tubing 304 for the syringe in sleeve 216A. Patient line 400 is a disposable kit, in one embodiment, such that connectors 402 and 404 may be connected to and removed from tubing connectors, such as connector 306, by the operator. In one embodiment, patient line 400 is a single-use disposable kit, such that it is connected to device 200 for one patient use, and then subsequently disconnected and discarded.

Connector 402 is operatively coupled to tubing 406, and connector 404 is operatively coupled to tubing 408. In one embodiment, connector 402 is coupled to the syringe in sleeve 216A, which contains contrast media, while connector 404 is coupled to the syringe in sleeve 216B, which contains a diluent such as saline. Thus, in this embodiment, contrast media is injected into tubing 406 of patient line 400, while diluent is injected into tubing 408. Tubing 406 and 408 are coupled to valve 416, which, in one embodiment, comprises an elastomeric-type valve that allows fluid flow from only one of tubing 406 and 408 to output tubing 417. In one embodiment, valve 416 comprises a one-way valve that allows fluid flow only in the direction towards output tubing 417. Guide rod 220 may help, in some cases, maintain the sterility of connectors 402 and 404 by aligning these connectors, during insertion, to prevent contact with non-sterile items.

As is shown in FIG. 4, tubing 408 is coupled to check valve 412 and transducer 414. In one embodiment, check valve 412 comprises a bi-directional check valve. Transducer 414 comprises a pressure transducer in one embodiment that is capable of measuring hemodynamic signals of a patient when patient line 400 is coupled a catheter that has been inserted into the patient. Transducer connector 410 may be coupled to device 200, such as by way of port 224 (FIG. 2B). When connected, hemodynamic signals generated by transducer 414 may be processed by a processor within device 200.

Output tubing 417 is coupled to stopcock 418 and to connector 420 shown in FIG. 4. Stopcock 418 may be manually manipulated by the operator to control fluid flow, and may also be connected to other external devices, such as a syringe. Connector 420 is used to connect patient line 400 to an external catheter that may deliver fluid to a patient. In one embodiment, connector 420 comprises a Luer-type connector.

In one embodiment, patient line 400 may also be used with device 100 shown in FIG. 1A. When used with device 100, transducer connector 410 is coupled to a mating port within device 100 (not shown), such that a processor of device 100 may process the hemodynamic signals. Assembly 401 may also be coupled in device 100 in this embodiment. Patient line 400 may be coupled to a manifold valve that is coupled to patient manifold sensor 114, such that connection port 402 may be coupled to tubing from the syringe, while connection port 404 may be coupled to tubing running through pump 106. In this embodiment, tubing 417 may also be coupled to, or run through, air detector 116 of device 100.

Figure 6A:
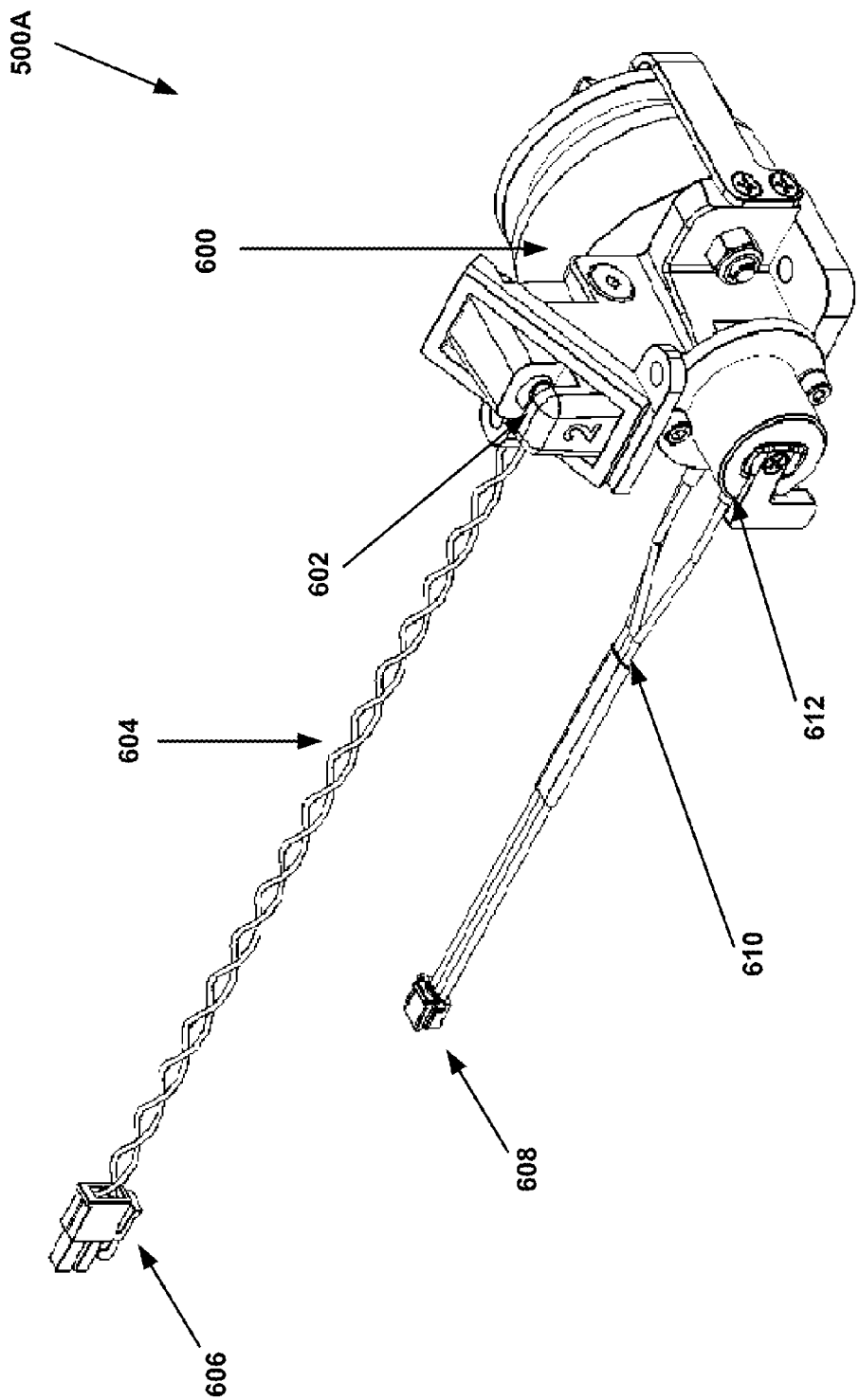
Figure 6C:
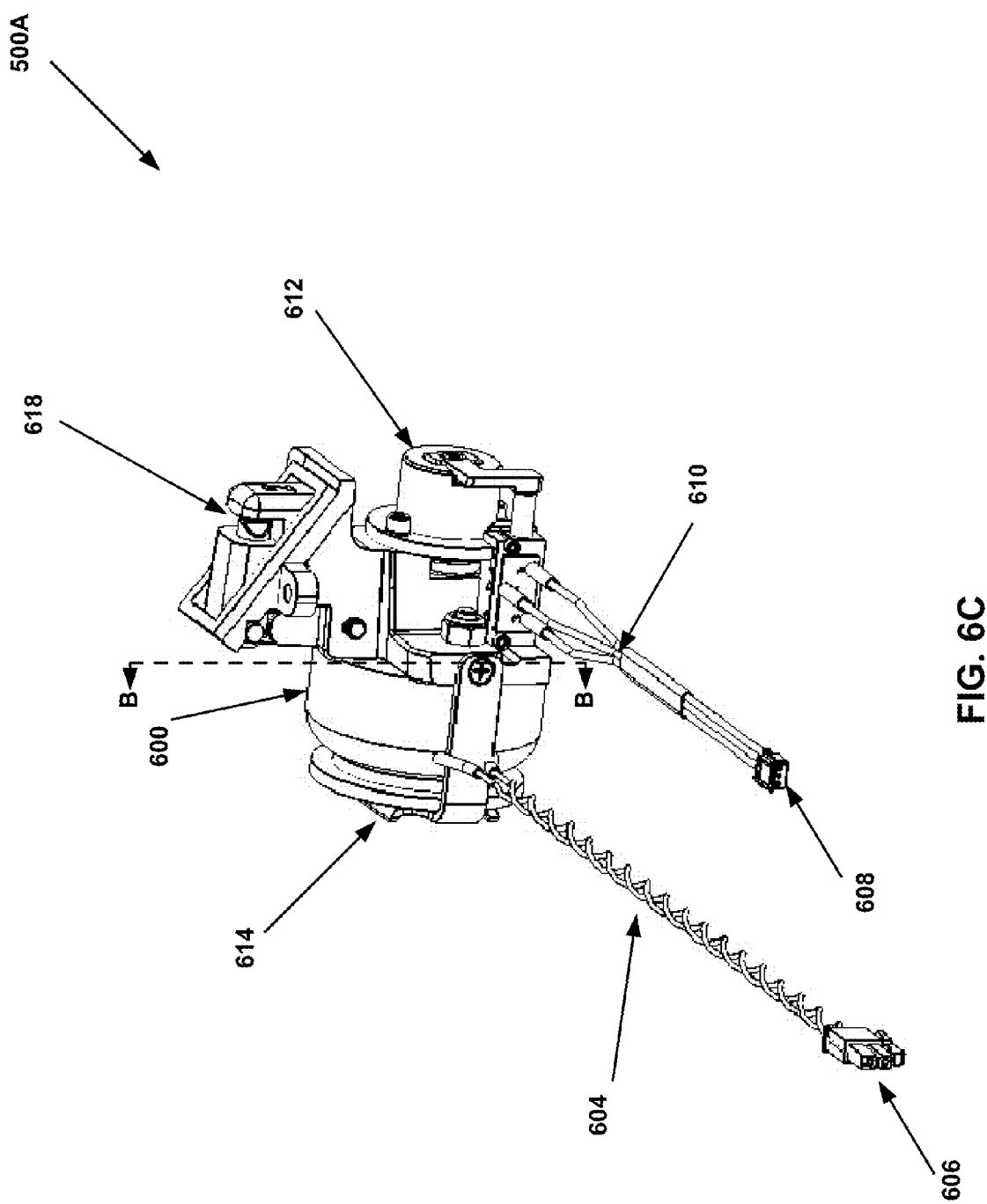

FIG. 5 is a perspective diagram of a bottom view of a portion of injector head 201 shown in FIG. 2D, according to one embodiment. The perspective diagram shown in FIG. 5 of this bottom view shows a number of different pinch valve mechanisms 500A, 500B, 502A, and 502B on the underside of injector head 201. Pinch valve mechanisms 500A and 502A are located beneath front-end assembly 218A, while pinch valve mechanisms 500B and 502B are located beneath front-end assembly 218B. FIGS. 6A-6C show perspective views of an example of an individual pinch valve mechanism, such as one or more of pinch valve mechanisms 500A, 500B, 502A, and 502B.

In one embodiment, pinch valve mechanisms 500A, 500B, 502A, and 502B each include one of pinch valves 232A, 232B, 234A, or 234B shown on the top side of injector head 201 in FIG. 2D. For example, pinch valve mechanisms 500A, 500B, 502A, and 502B may each include a tube pinching area that corresponds to one of pinch valves 232A, 232B, 234A, or 234B.

In one embodiment, one or more of pinch valve mechanisms 500A, 500B, 502A, and 502B, which are coupled to injector head 201, may comprise a plunger, a reciprocating arm driven by the plunger, and a tube pinching area, as will be described in more detail below. When a pinch valve mechanism 500A, 500B, 502A, and 502B is deactivated by injector head 201, it pinches closed, or seals off, fluid tubing that runs through its tube pinching area. As a result, in this embodiment, each pinch valve mechanism 500A, 500B, 502A, and 502B is capable of having a default state of being closed, where it seals off the fluid tubing that runs through its tube pinching area, and blocks any flow of fluid through the tubing. Each pinch valve mechanism 500A, 500B, 502A, and 502B may be in this default state when it is deactivated by injector head 201, such as when no power is delivered to the pinch valve mechanism.

In an alternate embodiment, each pinch valve mechanism 500A, 500B, 502A, and 502B is capable of having a default state of being open, where it opens a fluid path in the fluid tubing that runs through its pinching area. In this embodiment, when no power is delivered to the pinch valve mechanism, fluid is capable of flowing in the fluid path through the fluid tubing.

As can be seen from FIG. 5, the pinch valve mechanisms 500A, 500B, 502A, and 502B, as included within injector head 201, may provide a compact and/or relatively simple design. In some instances, pinch valve mechanisms 500A, 500B, 502A, and 502B may comprise solenoid-based mechanisms. In these instances, these mechanisms may be packaged inside the design space of injector head 201 with a few number of moving parts as compared with pneumatic-based pinch valves, and may also be provided at potentially lower cost, as well. In addition, solenoid-based mechanisms may be capable of providing very fast response time upon activation, due to the powerful magnetic field generated by the solenoid coils of these mechanisms when they are energized with relatively low power. Solenoid-based mechanisms may also provide strong pinching forces (e.g., when deactivated) to seal off high-pressure tubing that is coupled to pressurizing units, such as those contained within sleeves 216A and/or 216B.

FIGS. 6A-6C are perspective diagrams of various views of one of the pinch valve mechanisms 500A, 500B, 502A, or 502B shown in FIG. 5, according to one embodiment. For purposes of illustration only, it is assumed that the pinch valve mechanism shown in FIGS. 6A-6C is mechanism 500A, though any of the remaining pinch valve mechanisms 500B, 502A, and/or 502B may have a similar structure and functionality.

Pinch valve mechanism 500A may comprise a solenoid-based mechanism. As shown in FIG. 6A, pinch valve mechanism 500A may include a solenoid coil 600, a tube pinching area 602, an arbor 612, a wiring cable 604, a wiring cable 610, a connector 606, and a connector 608. Wiring cable 604 delivers power to solenoid coil 600 from injector head 201, and is coupled to connector 606. Connector 606 connects to a power-supplying component of injector head 201. Wiring cable 610 is coupled to connector 608, which is coupled to injector head 201.

Wiring cable 610 may be adapted to send information to injector head 201 regarding the status of tube pinching area 602 and/or the associated pinch valve. For example, in some cases, wiring cable 610 may send a signal to injector head 201 indicating that tube pinching area 602 and/or associated pinch valve is (a) open, (b) fully closed (i.e., with no tubing in tube pinching area 602), or (c) pinched closed (i.e., with tubing pinched in tube pinching area 602). Certain status information may be useful in various instances, such as providing safety-related feedback to injector head 201.

For instance, if injector head 201 is configured to perform (or determine whether to perform) a fill operation of medical fluid into a pressurizing unit contained within sleeve 216A or 216B, injector head 201 may review the status information provided by wiring cable 610 regarding the status of tube pinching area 602 and/or the associated pinch valve for pinch valve mechanism 500A that controls flow of fluid from a reservoir into the pressurizing unit. Injector head 201 would typically expect that tube pinching area 602 is open, such that fluid may flow from the reservoir into the pressurizing unit.

If, however, the status information indicates that tube pinching area 602 is pinched closed, injector head 201 may generate a safety-related error warning or indication to a user, indicating that the pinch valve is improperly closed during a fill operation. In some cases, injector head 201 may even terminate the fill operation until the situation is resolved. If the status information indicates that tube pinching area 602 is fully closed, injector head 201 may also generate an error warning or indication, or even terminate the fill operation. In this scenario, the fluid tubing may not be properly installed to run through tube pinching area 602 of pinch valve mechanism 500A. Injector head 201 may clear the error, or resume operation, after the situation has been resolved, such as by the user properly configuring the fluid tubing. In such fashion, injector head 201 may determine an operational state based upon the status of tube pinching area 602, such as a state that relates to a fluid fill (or even a fluid injection) operation. In some instances, injector head 201 may deactivate pinch valve mechanism 500A if it determines that the status information provided by wiring cable 610 is unexpected.

Injector head 201 may use a similar approach in analyzing the status information provided by wiring cable 610 when performing (or determining whether to perform) an injection operation. Injector head 201 may review the status information regarding the status of tube pinching area 602 and/or the associated pinch valve when pinch valve mechanism 500A that controls flow of fluid from a pressurizing unit into a patient line (e.g., patient line 400).

In some instances, injector head 201 may determine whether to perform a fill operation for a pressurizing unit based upon its review of status information for pinch valve mechanism 500A when pinch valve mechanism 500A controls a flow of fluid from the pressurizing unit into patient line 400A. To avoid the possibility of drawing back fluid from patient line 400A into the pressurizing unit, injector head 201 may expect that tube pinching area 602 to be pinched closed. If, however, the status information indicates that tube pinching area 602 is open, or even fully closed (indicating that no tubing is present), injector head 201 may generate an alarm or warning message, determine to delay the fill operation until the situation is resolved, or even deactivate pinch valve mechanism 500A.

Similarly, in some cases, injector head 201 may determine whether to perform an injection operation for a pressurizing unit based upon its review of status information for pinch valve mechanism 500A when pinch valve mechanism 500A controls a flow of fluid into the pressurizing unit from a reservoir. To avoid the possibility of injecting fluid back into the reservoir, injector head 201 may expect that tube pinching area 602 to be pinched closed. If, however, the status information indicates that tube pinching area 602 is open, or even fully closed (indicating that no tubing is present), injector head 201 may generate an alarm or warning message, determine to delay the injection operation until the situation is resolved, or even deactivate pinch valve mechanism 500A.

Figure 8:
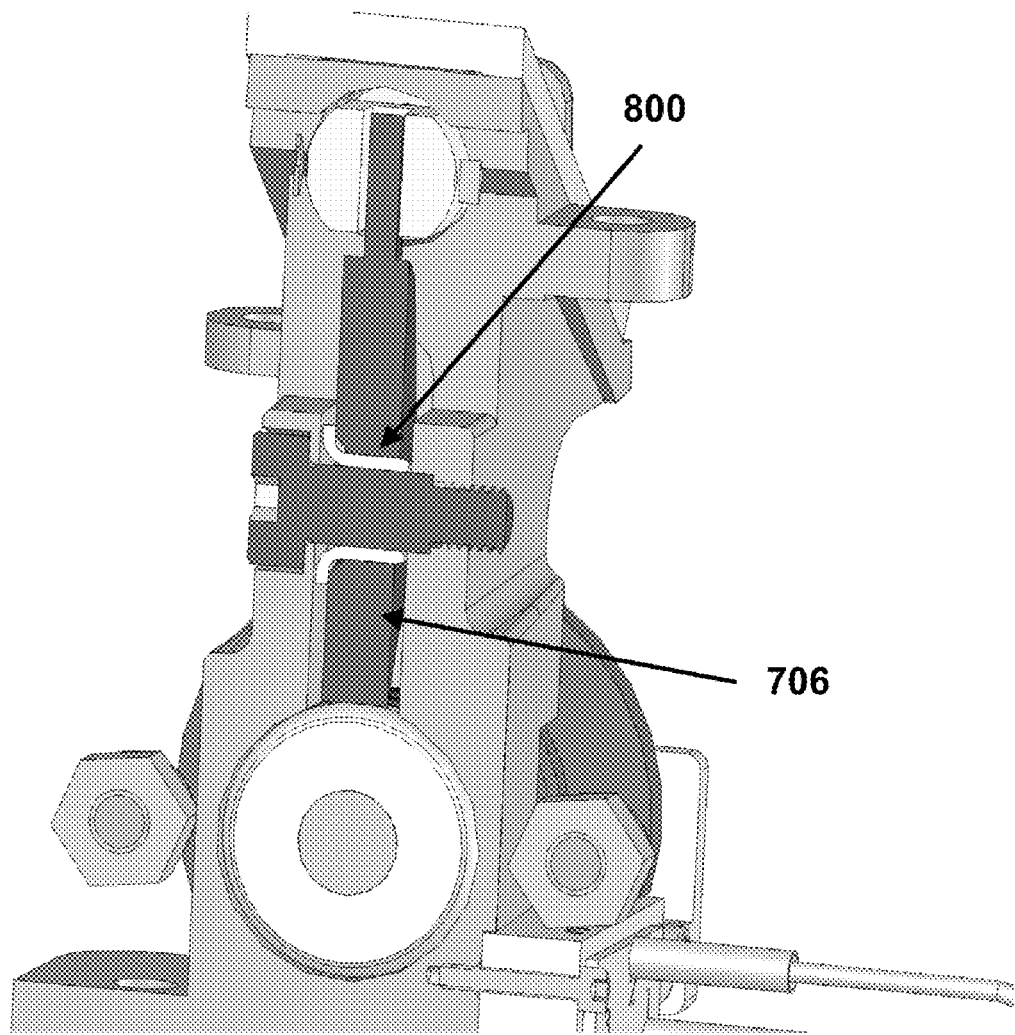
FIG. 8 is a sectional diagram illustrating a cross-sectional view of the pinch valve mechanism shown in FIG. 6C along line B-B, according to one embodiment.

When pinch valve mechanism 500A is deactivated (i.e., when it has no power), a spring (not shown) inside of pinch valve mechanism 500A may preload arbor 612, which then may preload a solenoid plunger (not shown), which is coupled to solenoid coil 600, with a determined pinch force. The solenoid plunger may then drive a reciprocating arm (not shown) that causes a pinching mechanism, such as one of pinch valves 232A, 232B, 234A, or 234B to pinch, and seal off, fluid tubing that runs through tube pinching area 602, as will be described in more detail below. FIG. 8 shows an example of some of the components not shown in FIG. 6A, such as the spring, solenoid plunger, and reciprocating arm.

When pinch valve mechanism 500A is activated by injector head 201, pinch valve mechanism 500A is configured to open a path in the fluid tubing that runs through tube pinching area 602, such that medical fluid is permitted to flow in the path of the fluid tubing. The plunger of pinch valve mechanism 500A may drive its reciprocating arm to open the path upon activation of pinch valve mechanism 500A by injector head 201. The fluid tubing may, in some instances, comprise a high-pressure tubing that is used to transport fluid at high pressures. For example, the fluid tubing may comprise a high-pressure braided tubing.

FIG. 6B illustrates a side perspective view of pinch valve mechanism 500A. This side view also shows a backstop bracket 614 of pinch valve mechanism 500A. Backstop bracket 614 may be used to secure pinch valve mechanism 500A within injector head 201. An example of a cross-sectional view of pinch valve mechanism 500A, along line A-A, is shown in FIG. 7, and is described in more detail below with reference to FIG. 7.

FIG. 6C illustrates another perspective view of pinch valve mechanism 500A. Certain details (e.g., of tube pinching area 602) may be seen more clearly in the perspective view of FIG. 6C. An example of a cross-sectional view of pinch valve mechanism 500A, along line B-B, is shown in FIG. 8, and is described in more detail below with reference to FIG. 8.

Figure 7:
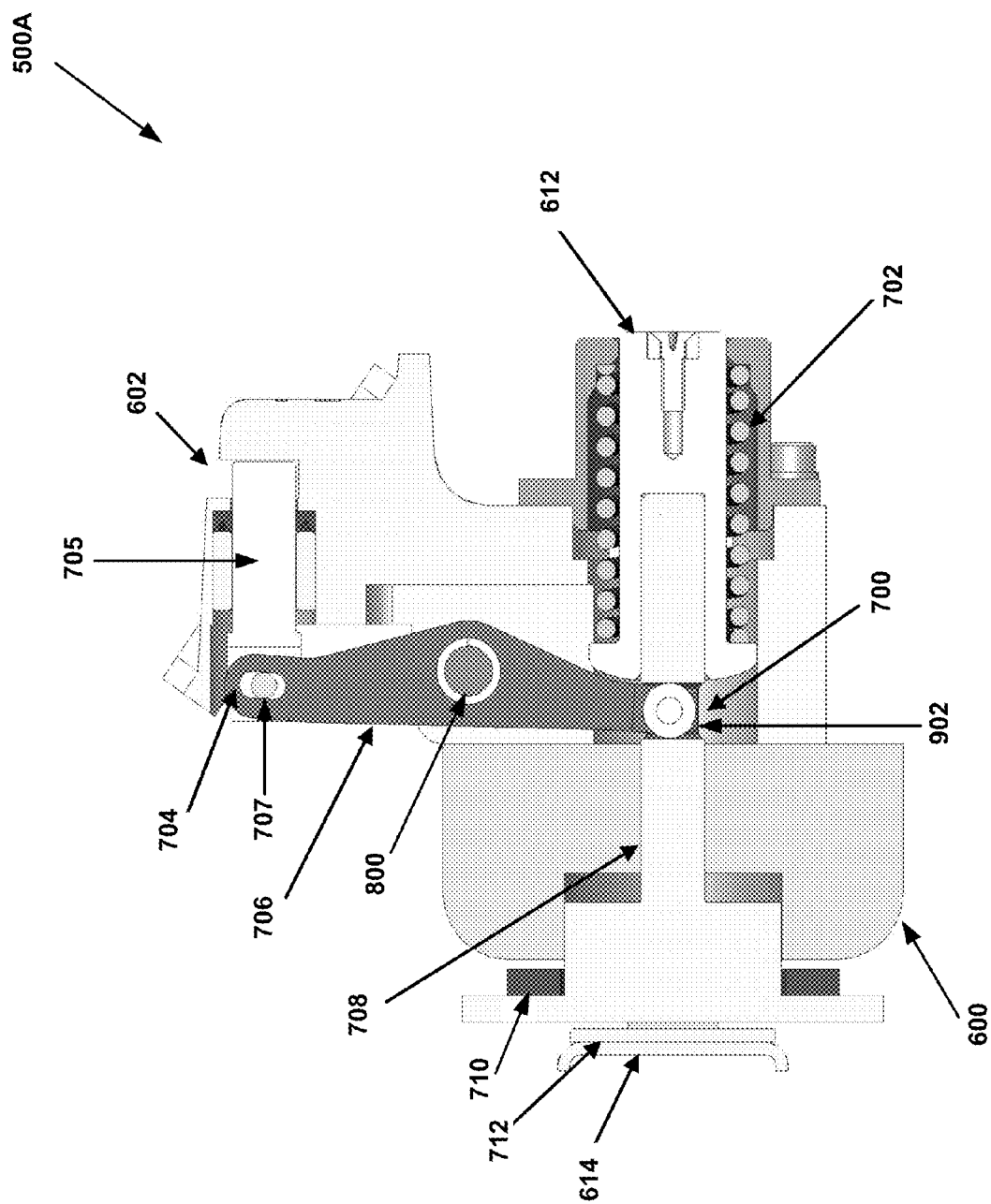
FIG. 7 is a sectional diagram illustrating a cross-sectional view of the pinch valve mechanism shown in FIG. 6B along line A-A, according to one embodiment.

FIG. 7 is a sectional diagram illustrating a cross-sectional view of the pinch valve mechanism 500A shown in FIG. 6B along line A-A, according to one embodiment. Again, for purposes of illustration only, FIG. 7 shows a cross-sectional view of pinch valve mechanism 500A. However, one or more of the remaining pinch valve mechanisms shown in FIG. 5, such as pinch valve mechanisms 500B, 502A, and/or 502B, may have a similar structure and functionality.

As shown in the example of FIG. 7, pinch valve mechanism 500A includes arbor 612 (FIGS. 6A-6C), a spring 702, a roller 700, tube pinching area 602, a slot 704, a reciprocating arm 706, solenoid coil 600, a solenoid plunger 708, a pad 710, a pad 712, and backstop bracket 614, which are all part of pinch valve mechanism 500A. One or more of such pads 710 and 712 may be coupled to solenoid plunger 708. Spring 702 may preload arbor 612, which is then capable of preloading solenoid plunger 708 with a determined amount of force. Solenoid plunger 708 may then drive reciprocating arm 706, which can pivot about a support bushing 800 (also shown in FIG. 8), which is also part of pinch valve mechanism 500A. The force of solenoid plunger 708 may be transferred to reciprocating arm 706 via roller 700. In some cases, roller 700 may be pinned to one end of reciprocating arm 706, and is capable of rotating inside a slot 902 (also shown in FIG. 9) of solenoid plunger 708.

Roller 700 may be a bi-directional roller, meaning that it is capable of rotating like a solid bearing when solenoid plunger 708 moves forward and backward. For example, roller 700 may rotate in a first direction within a slot (e.g., slot 902 shown in FIG. 9) of solenoid plunger 708 when solenoid plunger 708 moves forward. Roller 700 may rotate in a second, opposite direction within the slot of solenoid plunger 708 when solenoid plunger 708 moves backward. The direction of movement of solenoid plunger 708 may be controlled by activation and/or deactivation of solenoid coil 600 by injector head 201.

Force transfer from solenoid plunger 708 to reciprocating arm 706 may, in some cases, occur with low friction due to the rolling action of roller 700. Shaft-side loading of solenoid plunger 708 may also, in some cases, be minimized during activation of solenoid coil 600.

Friction between various moving parts within pinch valve mechanism 500A may also be decreased by other factors. For example, slot 704 (which may comprise a vertical slot) in reciprocating arm 706 may permit a pin 707 of pinch valve mechanism 500A to articulate in slot 704, reducing frictional binding that may manifest itself in a minimal surface area of contact.

In one embodiment, pinch arm 705 is capable of pinching, or sealing, any fluid tubing that runs through tube pinching area 602 when pinch valve mechanism 500A is in its default (de-energized) state. Spring 702 may preload arbor 612, which is then capable of preloading solenoid plunger 708 with a determined force. Solenoid plunger 708 may then drive reciprocating arm 706 via roller 700, which can pivot about the support bushing. Pin 707 articulates within slot 704, and causes pinch arm 705 to move (e.g., to the right in FIG. 7) and pinch the tubing in tube pinching area 602.

In one embodiment, injector head 201 delivers power to, and energizes, pinch valve mechanism 500A in order to open a fluid path in tubing that runs through tube pinching area 602, such that fluid may flow through the fluid path. Upon activation of solenoid coil 600, solenoid plunger 708 drives reciprocating arm 706 via roller 700, such that pin 707 articulates within slot 704, and causes pinch arm 705 to move (e.g., to the left in FIG. 7) and open the fluid path in the tubing running through tube pinching area 602.

FIG. 7 also shows pads 710 and 712 of pinch valve mechanism 500A. In one embodiment, pads 710 and 712 may comprise pads made of a poron material, or poron pads. In some cases, the poron pads may comprise poron washers. Pads 710 and 712 may help reduce an overall noise generated by pinch valve mechanism 500A. Pads 710 and 712 may help dampen, or de-accelerate, the high velocity motion of solenoid plunger 708. The noise generated by pinch valve mechanism 500A may, in some instances, be proportional to the rate of plunger dampening.

In one embodiment, the material used for reciprocating arm 706 may be a different type and/or grade of material than that used for roller 700. For example, reciprocating arm 706 may be made of a different type and/or grade of steel than roller 700 to prevent like materials from galling and/or seizing against one another. If stainless steel is not used, then an appropriate plating and/or coating may be implemented to help prevent corrosion.

FIG. 8 is a sectional diagram illustrating a cross-sectional view of pinch valve mechanism 500A shown in FIG. 6C along line B-B, according to one embodiment. FIG. 8 shows a portion of reciprocating arm 706 in cross section. FIG. 8 also shows bushing 800. Bushing 800 may protrude from reciprocating arm 706 on both ends. This may allow for minimal surface area contact with reciprocating arm 706, such that the remaining portion of reciprocating arm 706 may not introduce frictional contact with other mating parts.

Often, solenoid-based devices, such as pinch valves, provide limited stroke, or linear distance of travel, during electrical activation. In one embodiment, pinch valve mechanism 500A preserves the limited stroke afforded by solenoid-based operation. Reciprocating arm 706 may be implemented with a one-to-one load transfer characteristic (or a mechanical advantage of one, or substantially one) to preserve the limited stroke.

Figure 9:
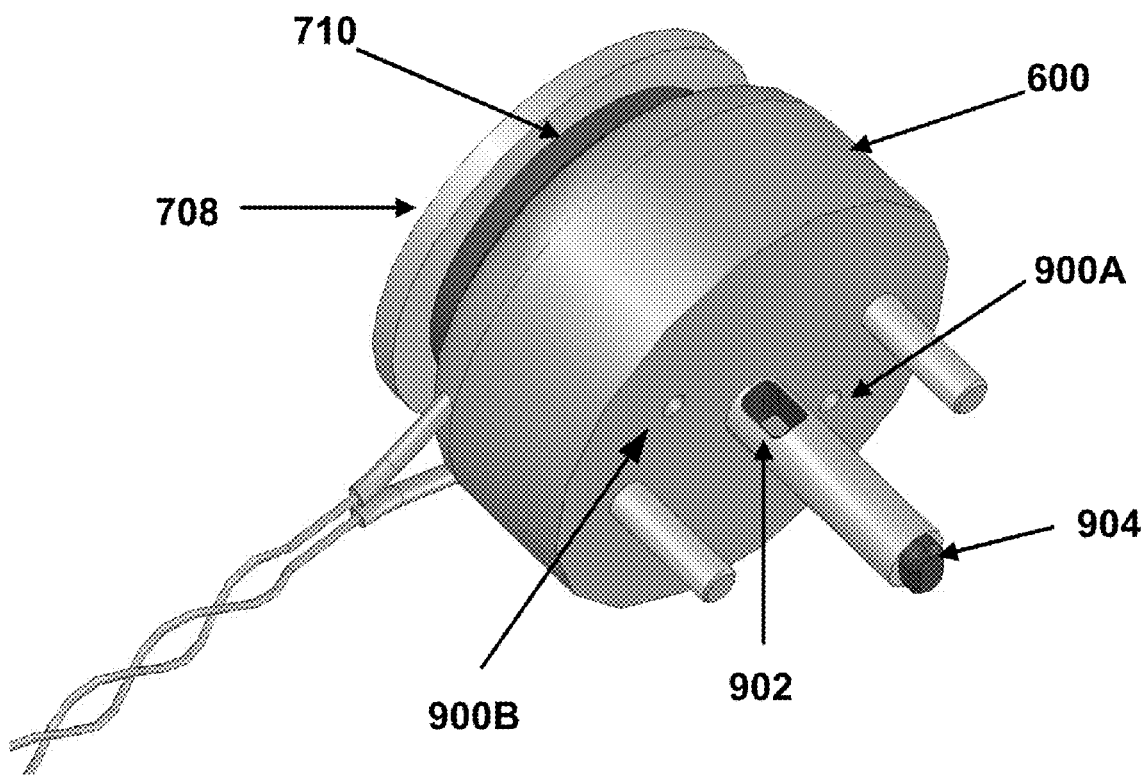
FIG. 9 is a perspective diagram of a portion of the pinch valve mechanism shown in FIGS. 6A-6C, according to one embodiment.

FIG. 9 is a perspective diagram of a portion of the pinch valve mechanism 500A shown in FIGS. 6A-6C, according to one embodiment. FIG. 9 shows pad 710, solenoid plunger 708, solenoid coil 600, alignment holes 900A and 900B, plunger slot 902, and plunger alignment shaft 904 (e.g., a vertical alignment shaft) for solenoid plunger 708. Alignment shaft 904 couples solenoid plunger 708 to reciprocating arm 706 and permits a bi-directional roller (e.g., roller 700 shown in FIG. 7) to rotate inside plunger slot 902 of solenoid plunger 708. Alignment holes 900A and 900B may be used to properly position and mount solenoid plunger 708, for example.

In one embodiment, friction between various moving parts within pinch valve mechanism 500A may be decreased by certain factors. Positioning plunger alignment shaft 904, as shown in FIG. 9, may help prevent metal from rubbing on metal as roller 700 rotates inside slot 902 of solenoid plunger 708.

The pinch valve mechanisms described herein, such as pinch valve mechanism 500A, 500B, 502A, and/or 502B may provide various benefits and advantages when used with injector head 201. For example, pinch valve mechanism 500A may be compact in size, as it may be packaged inside the design space of injector head 201 with minimal moving parts. In addition, pinch valve mechanism 500A may be reliable and quiet. As described previously, poron pads may be used to reduce noise levels during operation of the device. Also, pinch valve mechanism 500A is capable of providing a high-force sealing mechanism using a lower-power input source.

In some example instances, before actuation, pinch valve mechanism 500A is capable of closing against a thirty-five pound spring. However, when fully closed (i.e., when pinch arm 705 pinches off, or seals, tubing in tube pinching area 602), pinch valve mechanism 500A is capable of holding four-to-five times the thirty-five pound load when energized with electric current. This is due to the powerful magnetic field generated by solenoid coil 600 when it is energized with relatively low power. Since, in some instances, pinch valve mechanism 500A operates to have a default closed state, sealing off any tubing running through tube pinching area 602, spring 702 is capable of holding pinch arm 705 closed, and a relatively low amount of power supplied by injector head 201 may be needed to open, or hold open, pinch arm 705.

Figure 10:
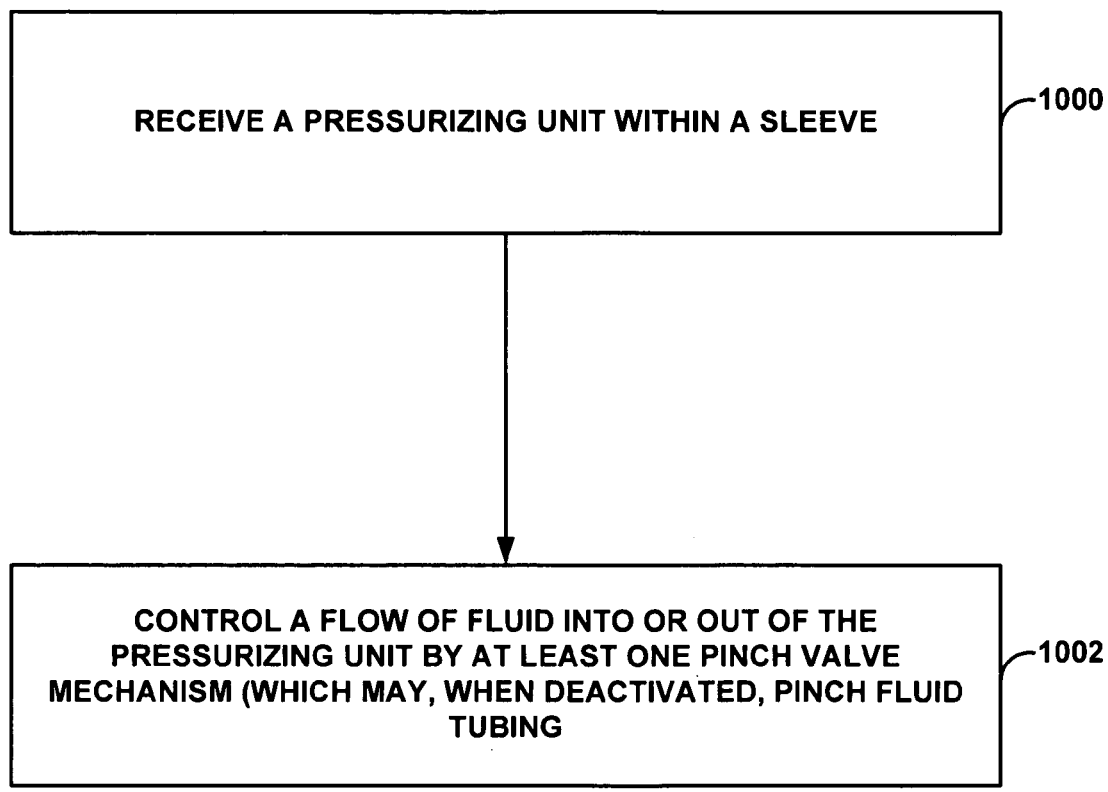
FIG. 10 is a flow diagram illustrating a method that may be performed by a powered medical fluid injection device, such as the device shown in FIGS. 1A-1B and/or the device shown in FIGS. 2A-2D, according to one embodiment.

FIG. 10 is a flow diagram illustrating a method that may be performed by a powered medical fluid injection device, such as device 100 shown in FIGS. 1A-1B and/or device 200 shown in FIGS. 2A-2D, according to one embodiment. For purposes of illustration only, it will be assumed in the description below that the method is performed by device 200.

Initially, device 200 receives a pressurizing unit within a sleeve, such as sleeve 216A or 216B (1000). For example, device 200 may received such a pressurizing unit (e.g., a syringe filled with medical fluid) into one of sleeves 216A or 216B upon insertion by an operator or use. During operation, device 200 may then control a flow of medical fluid into or out of the pressurizing unit through fluid tubing by at least one pinch valve mechanism (1002), such as one or more of pinch valve mechanisms 500A, 500B, 502A, and 502B. The at least one pinch valve mechanism may comprise a plunger (e.g., solenoid plunger 708 shown in FIG. 7), a reciprocating arm (e.g., reciprocating arm 706) driven by the plunger, and a tube pinching area (e.g., tube pinching area 602), and wherein the at least one pinch valve mechanism, when deactivated, is configured to cause the reciprocating arm to pinch the fluid tubing that runs through the tube pinching area. Device 200 may subsequently activate the at least one pinch valve mechanism, and, upon activation, drive the reciprocating arm with the plunger to open a path in the fluid tubing, such that medical fluid is permitted to flow in the path of the fluid tubing.

In some instances, the method performed by device 200 further includes loading the plunger with a determined amount of force by an arbor, the arbor being part of the at least one pinch valve mechanism. The arbor may be loaded by a spring in the at least one pinch valve mechanism, and device 200 may cause the reciprocating arm to pivot about a support bushing in the at least one pinch valve mechanism. In some instances, the method further includes rotating a bi-directional roller inside a slot of the plunger, the bi-directional roller being part of the at least one pinch valve mechanism and coupled to one end of the reciprocating arm. For example, when the plunger moves forward, the bi-directional roller may rotate in a first direction within the slot of the plunger. When the plunger moves backward, the bi-directional roller may rotate in a second, opposite direction within the slot of the plunger.

In some instances, the method may further include articulating a pin of the at least one pinch valve mechanism within a vertical slot of the reciprocating arm. Device 200 may reduce noise in the at least one pinch valve mechanism through use of one or more poron pads that are coupled to the plunger.

As described above, device 200 may activate the at least one pinch valve mechanism. In some instances, upon activation, the at least one pinch valve mechanism may open a path in fluid tubing that delivers medical fluid to the pressurizing unit contained within the sleeve of device 200 (e.g., during a fill operation). In some instances, upon activation, upon activation, the at least one pinch valve mechanism may open a path in fluid tubing that delivers medical fluid from the pressurizing unit contained within the sleeve (e.g, during an injection operation).

In some instances, device 200 may control the flow of medical fluid into the pressurizing unit with a first pinch valve mechanism (e.g. pinch valve mechanism 500A), and control a flow of medical fluid out of the pressurizing unit with a second pinch valve mechanism (e.g., pinch valve mechanism 502A). In one embodiment, device 200 may receive a second pressurizing unit within a second sleeve of device 200, and control a flow of medical fluid into or out of the second pressurizing unit through additional fluid tubing by at least one additional pinch valve mechanism. For example, device 200 may control the flow of medical fluid into the second pressurizing unit with a third pinch valve mechanism (e.g., pinch valve mechanism 500B), and control a flow of medical fluid out of the second pressurizing unit with a fourth pinch valve mechanism (e.g., pinch valve mechanism 502B).

Various embodiments have been described herein. These and other embodiments are within the scope of the following claims.

The invention claimed is:

1. A powered medical fluid injection device, comprising:
an injector head; and
at least one pinch valve mechanism coupled to the injector head, wherein the at least one pinch valve mechanism comprises a plunger, a reciprocating arm driven by the plunger, a tube pinching area, and a bi-directional roller coupled to one end of the reciprocating arm and configured to rotate inside a slot of the plunger,
wherein the at least one pinch valve mechanism, when deactivated by the injector head, is configured to pinch fluid tubing that runs through the tube pinching area.

2. The device of claim 1, wherein the plunger comprises a solenoid plunger.

3. The device of claim 1, wherein the at least one pinch valve mechanism, when activated by the injector head, is configured to open a path in the fluid tubing, such that medical fluid is permitted to flow in the path of the fluid tubing, and wherein the plunger drives the reciprocating arm to open the path upon activation of the at least one pinch valve mechanism by the injector head.

4. The device of claim 1, wherein the at least one pinch valve mechanism further comprises an arbor that is configured to load the plunger with a determined amount of force, and a spring that is configured to load the arbor.

5. The device of claim 1,
wherein the reciprocating arm is configured to pivot about the support bushing.

6. The device of claim 1, wherein the bi-directional roller rotates in a first direction within the slot of the plunger when the plunger moves forward, and wherein the bi-directional roller rotates in a second, opposite direction within the slot when the plunger moves backward.

7. The device of claim 1, wherein the plunger includes an alignment shaft to couple the plunger to the reciprocating arm and permit the bi-directional roller to rotate inside the slot of the plunger.

8. A powered medical fluid injection device, comprising:
an injector head; and
at least one pinch valve mechanism coupled to the injector head, wherein the at least one pinch valve mechanism comprises a plunger, a reciprocating arm driven by the plunger, and a tube pinching area, wherein the reciprocating arm includes a slot to permit a pin of the at least one pinch valve mechanism to articulate in the slot, and
wherein the at least one pinch valve mechanism, when deactivated by the injector head, is configured to pinch fluid tubing that runs through the tube pinching area.

9. The device of claim 1, wherein the at least one pinch valve mechanism further comprises one or more poron pads coupled to the plunger.

10. The device of claim 1, wherein the reciprocating arm provides a mechanical advantage of substantially one.

11. The device of claim 1, wherein the at least one pinch valve mechanism further comprises a pinch arm, coupled to the reciprocating arm, that is configured to pinch the fluid tubing that runs through the tube pinching area.

12. The device of claim 1, further comprising a sleeve configured to contain a pressurizing unit, and wherein the at least one pinch valve mechanism, when activated by the injector head, is configured to open a path in the fluid tubing that delivers medical fluid to the pressurizing unit.

13. The device of claim 1, further comprising a sleeve configured to contain a pressurizing unit, and wherein the at least one pinch valve mechanism, when activated by the injector head, is configured to open a path in the fluid tubing that delivers medical fluid from the pressurizing unit to an external patient line.

14. The device of claim 1, further comprising:
a first sleeve configured to contain a first pressurizing unit; and
a second sleeve configured to contain a second pressurizing unit,
wherein the at least one pinch valve mechanism comprises a first pinch valve mechanism configured to be coupled to first fluid tubing into the first pressurizing unit, a second pinch valve mechanism configured to be coupled to second fluid tubing out of the first pressurizing unit, a third pinch valve mechanism configured to be coupled to third fluid tubing into the second pressurizing unit, and a fourth pinch valve mechanism configured to be coupled to fourth fluid tubing out of the second pressurizing unit.

15. The device of claim 1, wherein the at least pinch valve mechanism further comprises a cable that is configured to send information to the injector head regarding a status of the tube pinching area, and wherein the status of the tube pinching area indicates whether the tube pinching area is either open, pinched closed, or fully closed.

16. The device of claim 15, wherein the injector head is configured to determine an operational state based upon the status of the tube pinching area, and wherein the operational state comprises a state related to a fluid fill or a fluid injection operation.

17. The device of claim 15, wherein the injector head is configured to deactivate the at least one pinch valve mechanism based upon the status of the tube pinching area.

18. A pinch valve mechanism, comprising:
a plunger;
a reciprocating arm driven by the plunger;
a tube pinching area; and
a bi-directional roller coupled to one end of the reciprocating arm and configured to rotate inside a slot of the plunger,
wherein the pinch valve mechanism, when deactivated, is configured to pinch tubing that runs through the tube pinching area.

19. A method comprising:
receiving a pressurizing unit within a sleeve of a powered medical fluid injection device;

controlling a flow of medical fluid into or out of the pressurizing unit through fluid tubing by at least one pinch valve mechanism, wherein the at least one pinch valve mechanism comprises a plunger, a reciprocating arm driven by the plunger, a bi-directional roller coupled to one end of the reciprocating arm that is configured to rotate inside a slot of the plunger, and a tube pinching area, and wherein the at least one pinch valve mechanism, when deactivated, is configured to cause the reciprocating arm to pinch the fluid tubing that runs through the tube pinching area.

20. The method of claim 19, wherein the plunger comprises a solenoid plunger.

21. The method of claim 19, further comprising:
activating the at least one pinch valve mechanism; and
upon activation, driving the reciprocating arm with the plunger to open a path in the fluid tubing, such that medical fluid is permitted to flow in the path of the fluid tubing.

22. The method of claim 19, further comprising:
loading the plunger with a determined amount of force by an arbor, the arbor being part of the at least one pinch valve mechanism; and
loading the arbor by a spring in the at least one pinch valve mechanism.

23. The method of claim 19, further comprising:
pivoting the reciprocating arm about a support bushing in the at least one pinch valve mechanism.

24. The method of claim 19, wherein rotating the bi-directional roller comprises:
when the plunger moves forward, rotating the bi-directional roller in a first direction within the slot of the plunger; and
when the plunger moves backward, rotating the bi-directional roller in a second, opposite direction within the slot of the plunger.

25. A method comprising:
receiving a pressurizing unit within a sleeve of a powered medical fluid injection device;
controlling a flow of medical fluid into or out of the pressurizing unit through fluid tubing by at least one pinch valve mechanism, wherein the at least one pinch valve mechanism comprises a plunger, a reciprocating arm driven by the plunger, and a tube pinching area, and wherein the at least one pinch valve mechanism, when deactivated, is configured to cause the reciprocating arm to pinch the fluid tubing that runs through the tube pinching area; and
articulating a pin of the at least one pinch valve mechanism within a slot of the reciprocating arm.

26. The method of claim 19, further comprising reducing noise in the at least one pinch valve mechanism through use of one or more poron pads that are coupled to the plunger.

27. The method of claim 19, further comprising:
activating the at least one pinch valve mechanism; and
upon activation, opening a path in fluid tubing that delivers medical fluid to the pressurizing unit contained within the sleeve of the powered medical fluid injection device.

28. The method of claim 19, further comprising:
activating the at least one pinch valve mechanism; and
upon activation, opening a path in fluid tubing that delivers medical fluid from the pressurizing unit contained within the sleeve of the powered medical fluid injection device to an external patient line.

29. The method of claim 19, further comprising: receiving a second pressurizing unit within a second sleeve of the powered medical fluid injection device; and
controlling a flow of medical fluid into or out of the second pressurizing unit through additional fluid tubing by at least one additional pinch valve mechanism.

30. The method of claim 29, wherein:
controlling the flow of medical fluid into or out of the pressurizing unit comprises controlling a flow of medical fluid into the pressurizing unit with a first pinch valve mechanism, and controlling a flow of medical fluid out of the pressurizing unit with a second pinch valve mechanism; and
controlling the flow of medical fluid into or out of the second pressurizing unit comprises controlling a flow of medical fluid into the second pressurizing unit with a third pinch valve mechanism, and controlling a flow of medical fluid out of the second pressurizing unit with a fourth pinch valve mechanism.

31. The method of claim 19, further comprising sending information to the injection device regarding a status of the tube pinching area, wherein the status of the tube pinching area indicates whether the tube pinching area is either open, pinched closed, or fully closed.

32. The method of claim 31, further comprising determining an operational state based upon the status of the tube pinching area, wherein the operational state comprises a state related to a fluid fill or a fluid injection operation.

33. The method of claim 31, further comprising deactivating the at least one pinch valve mechanism based upon the status of the tube pinching area.

34. A powered medical fluid injection device, comprising:
receiving means for receiving a pressurizing unit; and
controlling means for controlling a flow of medical fluid into or out of the pressurizing unit through fluid tubing, wherein the controlling means comprises a plunger, a reciprocating arm driven by the plunger, and a bi-directional roller coupled to one end of the reciprocating arm that is configured to rotate inside a slot of the plunger, wherein the controlling means, when deactivated, pinches the fluid tubing to prohibit the flow of medical fluid in the fluid tubing.

* * * * *